United States Patent [19]

Babu et al.

[11] Patent Number: 5,602,277
[45] Date of Patent: Feb. 11, 1997

[54] SUBSTITUTED BENZENE DERIVATIVES USEFUL AS NEURAMINIDASE INHIBITORS

[75] Inventors: Yarlagadda S. Babu; Pooran Chand; David A. Walsh, all of Birmingham, Ala.

[73] Assignee: BioCryst Pharmaceuticals, Inc., Birmingham, Ala.

[21] Appl. No.: 413,886

[22] Filed: Mar. 30, 1995

[51] Int. Cl.$^6$ .................. C07C 279/18; A61K 31/19
[52] U.S. Cl. .................. 562/439; 514/381; 514/535; 514/538; 514/541; 514/542; 514/544; 514/562; 514/563; 514/564; 514/565; 514/567; 514/568; 514/625; 514/634; 514/635; 560/34
[58] Field of Search ................ 562/439; 560/34; 514/563, 542, 381, 535, 538, 541, 542, 544, 562, 563, 564, 565, 567, 568, 625, 634, 635

[56] References Cited

U.S. PATENT DOCUMENTS 4,487,725  12/1984  Arndt et al. ............... 260/507 R
5,453,533  9/1995   Luo et al. .................. 560/142
5,512,596  4/1996   Kim et al. .................. 514/568

FOREIGN PATENT DOCUMENTS 0539204     4/1993   European Pat. Off. .
91/16320    10/1991  WIPO .
WO92/08464  5/1992   WIPO .
93/12105    6/1993   WIPO .

OTHER PUBLICATIONS

Journal Chemical Society, Perkin Transactions II, vol. 2, issued 1979, J. Kaczmarek et al., "A Correlation of Substituent Effects with the Acidity of Aromatic Tetrazolic Acids," pp. 1670–1674.

Journal of Organic Chemistry, vol. 35, No. 5, issued May 1970, T. Nishiguchi et al., "Electronic Effects of the Substituents Containing the Thiocarbonyl Group," pp. 1591–1593.

Polish Journal of Chemistry, vol. 54, issued 1980, J. Kruszewski et al., "Analysis of Ultraviolet Spectra of Substituted 5–Phenyltetrazoles," pp. 925–937.

Chemical Abstracts, vol. 112, issued 1990, Goedecke A.–G., "N–(o–aminophenyl) benzamides as neoplasm inhibitors," abstract 118467s, AT 388,913 (25 Sep. 1989).

Chemical Abstracts, vol. 94, issued 1981, J. Horyna, "N–acylaminoarylsufonic acids" abstract 67284e, CZ 183, 139 (15 May 1980).

Chemical Abstracts, vol. 94, issued 1981, F. H. Lee et al., "Bioavailability and metabolism of potassium phosphanilate in laboratory animals and humans," p. 10, col. 2, abstact 41113y, Antimicrob. Agents Chemother, 18(5), pp. 746–752.

Chemical Abstracts, vol. 101, issued 1984, A. Pinelli et al., "Inhibitory effects of 2–guanidinebenzimidazole and 1–phenylbiguanide on gastric acid secretion in rats," abstract 163490c, Arzneim. Forsch. 34(8), pp. 890–894.

Biochemistry, vol. 34, No. 10, issued 1995, M. J. Jedrzejas et al., "Structures of Aromatic Inhibitors of Influenza Virus Neuraminidase," pp. 3144–3151.

Singh et al., Structure–Based Inhibitors of Influenza Virus Sialidase. A Benzoic Acid Lead With Novel Interaction, J. Med. Chem. 1995, vol. 38, No. 17, pp. 3217–3225.

Williams, et al., Synthesis And Influenza Neuraminidase Inhibitory Activity Of Aromatic Analogues of Sialic Acid, Bioorganic & Medicinal Chemistry Lasers, vol. 5, No. 19, pp. 2251–2254, 1995.

International Workshop on Sialidases from Viruses, Bacteria, Parasites and Mammalian Sources, Rigi Kaltbad Switzerland, Apr. 18–19, 1994, abstract from meeting, Ming Luo et al.

*Primary Examiner*—Gary Geist
*Assistant Examiner*—Barbara S. Frazier
*Attorney, Agent, or Firm*—Pollock, Vande Sande & Priddy

[57] ABSTRACT

A compound of the Formula (I):

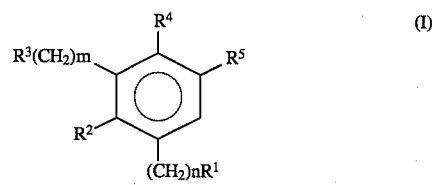

or pharmaceutically-suitable salts or prodrug forms thereof, wherein:

n is 0–1;

m is 0;

p is 0–1;

$R^1$ is —$CO_2H$;

$R^2$ is selected from the group consisting of H, —OH, and —$NH_2$;

$R^3$ is H;

$R^4$ is —C(O)NHR$^8$;

$R^5$ is —NHC(R$^6$)NH$_2$ $R^6$ is selected from the group consisting of =NH, =NOH, =NCN, =O, and =S; and $R^8$ is selected from the group consisting of $C_1$–$C_4$ linear or branched alkyl substituted with 0–3 halogens on each carbon.

25 Claims, No Drawings

SUBSTITUTED BENZENE DERIVATIVES USEFUL AS NEURAMINIDASE INHIBITORS

FIELD OF THE INVENTION

This invention relates to novel substituted benzene compounds and derivatives thereof useful as neuraminidase inhibitors, to pharmaceutical compositions containing said compounds, and to methods of using said compounds, useful for the prevention, treatment, or amelioration of viral and other infections.

BACKGROUND OF THE INVENTION

Influenza viruses consist of eight pieces of single stranded RNA, packaged in orderly fashion within the virion. Each piece codes for one of the major viral proteins. The replication complex is enclosed within a membrane composed of matrix protein associated with a lipid bilayer. Embedded in the lipid bilayer are two surface glycoprotein spikes, hemagglutinin (HA) and the enzyme neuraminidase (NA). All of the viral genes have been cloned and the three-dimensional structures of the surface glycoproteins have been determined.

Despite the wealth of information available, influenza remains a potentially devastating disease of man, lower mammals, and birds. No effective vaccine exists and no cure is available once the infection has set in.

Influenza viruses continually undergo antigenic variation in the two surface antigens, HA and NA, toward which neutralizing antibodies are directed. For this reason, vaccines and a subject's natural immune system have not been very effective. Attention is now being directed to finding other potential antiviral agents acting at other sites of the virion. This invention is directed to novel compounds which are useful in inhibiting the viral surface enzyme NA.

Furthermore, many other organisms carry NA. Many of these NA-possessing organisms are also major pathogens of man and/or mammals, including *Vibrata choleral, Clostridium perfringes, Streptococcus pneumonia, Arthrobacter sialophilas,* and other viruses such as parainfluenza virus, mumps virus, Newcastle disease virus, fowl plague virus, and Sendai virus. Compounds of this invention are also directed to inhibiting NA of these organisms.

In viruses, NA exists as a tetramer made of four roughly spherical subunits and a centrally-attached stalk containing a hydrophobic region by which it is embedded in the organism's membrane. Several roles have been suggested for NA. The enzyme catalyzes cleavage of the α-ketosidic linkage between terminal sialic acid and an adjacent sugar residue. Removal of the sialic acid lowers the viscosity and permits access of the virus to the epithelial cells. NA also destroys the HA receptor on the host cell, thus allowing elution of progeny virus particles from infected cells. In general, the role of NA is thought to be for the mobility of the virus both to and from the site of infections. Compounds that inhibit neuraminidase's activity may protect a subject from infection and/or cure a subject once infection has set in. It is a further object of this invention to provide a method of using compounds of this invention for treating and/or curing a viral infection.

Analogs of neuraminic acid, such as 2-deoxy-2,3-didehydro-N-acetylneuraminic acid (DANA) and its derivatives are known to inhibit HA in vitro; however, these compounds are inactive in vivo. Palese and Schulman, in *Chemoprophylaxis and Virus Infection of the Upper Respiratory Tract,* Vol. 1 (J. S. Oxford, Ed.), CRC Press, 1977, at PS 189–205.

Von Itzstein et al. describes cyclohexane analogs of α-D-neuraminic acid of the formula:

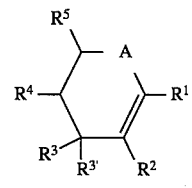

and

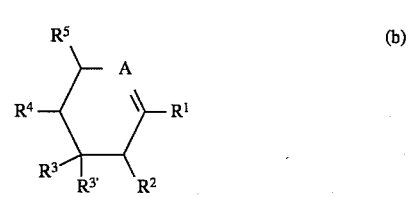

wherein:

A is O, C, or S in Formula (a), and N or C in Formula (b);

$R^1$ is $CO_2H$, $PO_3H_2$, $NO_2$, $SO_2$, $SO_3H$, tetrazolyl-, $CH_2CHO$, CHO, or $CH(CHO)_2$;

$R^2$ is H, $OR^6$, F, Cl, Br, CN, $NHR^6$, $SR^6$ or $CH_2X$, where X is $NHR^6$ halogen, or $OR^6$;

$R^3$ and $R^{3'}$ are H, CN, $NHR^6$, $N_3$, $SR^6$, $=NOR^6$, $OR^6$, guanidino, $NR^6$;

$R^4$ is $NHR^6$, $SR^6$, $OR^6$, $CO_2R^6$, $NO_2$, $C(R^6)_3$, $CH_2CO_2R^6$, $CH_2NO_2$, or $CH_2NHR^6$;

$R^5$ is $CH_2YR^6$, $CHYR^6CH_2YR^6$ or $CHYR^6CHYR^6CH_2YR^6$;

$R^6$ is H, acyl, alkyl, allyl, or aryl;

Y is O, S, NH, or H, and pharmaceutical salts thereof; useful as antiviral agents. This reference does not disclose aromatic derivatives of the present invention.

SUMMARY OF THE INVENTION

An embodiment of the invention is directed to novel benzene compounds useful for the treatment of influenza. These compounds have the formula:

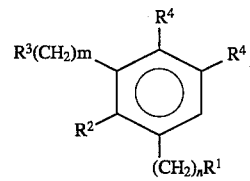

or pharmaceutically-suitable salts or prodrug forms thereof, wherein:

n is 0–1:

m is 0–3;

p is 0–1;

$R^1$ is selected from the group consisting of $-CO_2H$, $-SO_2H$, $-SO_3H$, $-PO_3H_2$, and tetrazolyl;

$R^2$ is selected from the group consisting of H, $-OH$, and $-NH_2$;

$R^3$ is selected independently at each occurrence from the group consisting of $-OR$, $-N(R)_2$, $-N_3$, $-NHC(R^6)NH_2$, $-CN$ $-C(R^6)NH_2$, H, $-C(R)(=N)NHC(=NH)NH_2$, $-C(=N)RC(=NH)NH_2$, NHCN, and $CH=NOH$;

$R^4$ is selected from the group consisting of H, —OR, —(CH$_2$)$_p$NHR$^7$ and —C(O)NHR$^8$;

$R^5$ is selected from the group consisting of H, —R$^3$, —(CH(R$^3$))$_n$$_m$CH$_2$R$^3$, —NHC(R$^6$)NH$_2$, —CH=CHCH$_2$R$^3$, NHCN, and CH=NOH;

$R^6$ is selected from the group consisting of =NH, =NOH, =NCN, =O, and =S;

$R^7$ is selected from the group consisting of —C(=Y)R$^8$, —S(O$_2$)R, —C(O)OR$^8$, —C(=Y)NHR$^8$, and —CH$_2$C(=Y)R$^8$;

$R^8$ is selected from the group consisting of C$_1$-C$_4$ linear or branched alkyl substituted with 0-3 halogens on each carbon;

R is selected from the group consisting of H, C$_1$-C$_4$ linear or branched alkyl, C$_1$-C$_4$ linear or branched alkyl-OH, C$_1$-C$_4$ linear or branched alkyl-NH$_2$;

Y is O or S;

with the following provisos:
1. When $R^1$ is CO$_2$H, SO$_3$H, or PO$_3$H$_2$, and $R^4$ is (CH$_2$)$_p$NHR$^7$, then $R^2$, $R^3$, and $R^5$ cannot all be H;
2. The number of substituents on the aromatic ring cannot exceed four.

Preferred compounds of this invention are compounds of Formula (I) or pharmaceutically-suitable salts or prodrug forms thereof, wherein:

$R^1$ is CO$_2$H;

$R^2$ is H;

$R^3$ is selected from the group consisting of H, —OR, —NHC(R$^6$)NH$_2$, NHCN, and CH=NOH;

$R^4$ is selected from the group consisting of H, —OR, —(CH$_2$)$_p$NHR$^7$, and —C(O)NHR$^8$;

$R^5$ is selected from the group consisting of H, —CH(R$^3$)$_2$CH$_2$OR, —CH$_2$OR, —NHC(R$^6$)NH$_2$, —CH=CHCH$_2$OR, —NHCN, and CH=NOH;

$R^6$ is selected from the group consisting of =NH, =NOH, =NCN, =O, and =S;

$R^7$ is selected from the group consisting of —C(=Y)R$^8$, —S(O$_2$)R, —C(O)OR$^8$, —C(=Y)NHR$^8$, and —CH$_2$C(=Y)R$^8$;

$R^8$ is selected from the group consisting of C$_1$-C$_4$ linear or branched alkyl substituted with 0-3 halogens on each carbon;

m is 0-2; and p is 0, with the following provisos:
1. When $R^1$ is CO$_2$H, and $R^4$ is (CH$_2$)$_p$NHR$^7$, then $R^2$, $R^3$, and $R^5$ cannot all be H; and
2. The number of substituents on the aromatic ring cannot exceed four.

More preferred compounds are compounds of Formula (I) or pharmaceutically-suitable salts or prodrug forms thereof, wherein:

$R^1$ is CO$_2$H;

$R^2$ is H;

$R^3$ is selected from the group consisting of H, —OH, —NHC(=NH)NH$_2$, NHCN, and CH=NOH;

$R^4$ is H, —OH, —OCH$_3$, —NHCOCH$_3$, —NHSO$_2$CH$_3$, and C(O)NHCH$_3$;

$R^5$ is H, —CH$_2$CH(OH)CH$_2$OH, —CH$_2$OH, —NHC(=NH)NH$_2$, and —CH=CHCH$_2$OH, —NHCN, CH=NOH; and m is 0-2;

with the following provisos:
1. When $R^1$ is CO$_2$H, and $R^4$ is (CH$_2$)$_p$NHR$^7$, then $R^2$, $R^3$, and $R^5$ cannot all be H; and
2. The number of substituents on the aromatic ring cannot exceed four.

Specifically preferred compounds of this invention are the following, or pharmaceutically-suitable salts or prodrug forms thereof:

Phenylguanidine;
1-Phenylbiguanide;
4-Acetylaminobenzoic acid;
4-Acetylaminobenzenesulfonic acid;
4-Acetylaminophenylphosphoric acid;
4-(Trifluoroacetamido)benzoic acid;
4-Thioacetamidobenzoic acid;
4-[(Methylsulfonyl)amino]benzoic acid;
3-Guanidinobenzoic acid;
3-[Amino(cyanoimino)methyl]aminobenzoic acid;
3-Cyanoaminobenzoic acid;
3-(2-Amino-2-imino)ethylbenzoic acid;
4-(Acetamino)phenylacetic acid;
4-(Methylaminocarbonyl)benzoic acid;
4-Acetylamino-3-hydroxymethylbenzoic acid;
β-(2-N-Acetylamino-5-carboxyphenyl)ethanol
4-Acetylamino-3-(2',3'-dihydroxypropyl)benzoic acid;
4-Acetylamino-3-aminobenzoic acid;
4-Acetylamino-3-[(aminoiminomethyl)amino]benzoic acid;
3-[(Aminoiminomethyl)amino]-4-(2-methylpropionylamino)benzoic acid;
4-Acetylamino-3-[(hydroxylimino)methyl]benzoic acid;
3-[(Aminoiminomethyl)amino]-4-[(methylsulfonyl)amino]benzoic acid;
3-[(N-Hydroxyimino)methyl]-4-[(methylsulfonyl)amino] benzoic acid;
3-[((Aminoimino)methyl)amino]-4-methoxybenzoic acid;
3-[(Aminoiminomethyl)amino]-4-hydroxybenzoic acid;
3,5-Bis-[(aminoiminomethyl)amino]benzoic acid;
3-Amino-5-{[(aminoimino)methyl]amino}benzoic acid;
3-[(Aminoiminomethyl)amino]-5-[(N-hydroxylimino)methyl]benzoic acid; and
3-[(Aminoiminomethyl)amino-5-hydroxymethyl)-4-(methylsulfonyl)aminobenzoic acid.

In the present invention, it has been discovered that the compounds of Formula (I) above are useful as inhibitors of viral neuraminidase and neuraminidase from other pathogenic organisms, and for the prevention, treatment, or amelioration of viral and other infections.

A further embodiment of this invention is directed to pharmaceutical compositions containing a compound of Formula (I) useful for the prevention, treatment, or amelioration of a viral infection.

Still a further embodiment of this invention is directed to methods for preventing, treating, or ameliorating viral infections comprising administering to a host infected with such virus a therapeutically effective amount of one or more compounds of Formula (I) as described above.

The compounds herein described may have asymmetric centers. All chiral, diastereomeric, and racemic forms are included in the present invention. Many geometric isomers of olefins, C=N double bonds, and the like can also be present in the compounds described herein, and all such stable isomers are contemplated in the present invention.

When any variable (for example, R through $R^8$, m, n, p, etc.) occurs more than one time in any constituent or in Formula (I) or any other formula herein, its definition on each occurrence is independent of its definition at every other occurrence. Also, combinations of substituents and/or variables are permissible only if such combinations result in stable compounds.

As used herein and in the claims, "alkyl" is intended to include both branched and straight-chain saturated aliphatic hydrocarbon groups having the specified number of carbon atoms; "alkoxy" represents an alkyl group of indicated number of carbon atoms attached through an oxygen bridge; "cycloalkyl" is intended to include saturated ring groups, such as cyclopropyl, cyclobutyl, cyclopentyl, cyclohexyl, cycloheptyl, and cyclooctyl; and "bicycloalkyl" is intended to include saturated bicyclic ring groups such as [3.3.0] bicyclooctane, [4.3.0]bicyclononane, [4.4.0]bicyclodecane (decalin), [2.2.2]bicyclooctane, and so forth. "Halogen," as used herein and in the claims, refers to fluoro, chloro, bromo, and iodo; and "counterion" is used to represent a small, negatively-charged species such as chloride, bromide, hydroxide, acetate, sulfate, and the like.

As used herein and in the claims, "aryl" or "aromatic residue" is intended to mean phenyl or naphthyl; "carbocyclic" is intended to mean any stable 5- to 7-membered monocyclic or bicyclic or 7- to 14-membered bicyclic or tricyclic carbon ring, any of which may be saturated, partially unsaturated, or aromatic; for example, indanyl or tetrahydronaphthyl (tetralin).

The term "substituted," as used herein and in the claims, means that a one or more hydrogen on the designated atom is replaced with a selection from the indicated group, provided that the designated atom's normal valency is not exceeded, and that the substitution results in a stable compound.

By "stable compound" or "stable structure" is meant herein a compound that is sufficiently robust to survive isolation to a useful degree of purity from a reaction mixture, and formulation into an efficacious therapeutic agent.

As used herein and in the claims, "therapeutically effective amount" refers to that amount necessary to administer to a host to achieve the desired result of inhibiting the enzyme neuraminidase to prevent, treat, or ameliorate a viral or other infection.

As used herein and in the claims, "pharmaceutically-suitable salts and prodrugs" refers to derivatives of the disclosed compounds that are modified by making acid or base salts, or by modifying functional groups present in the compounds in such a way that the modifications are cleaved, either in routine manipulation or in vivo, to the parent compounds. Examples include, but are not limited to, mineral or organic acid salts of basic residues such as amines; alkali or organic salts of acidic residues such as carboxylic acids; acetate, formate, and benzoate derivatives of alcohols and amines; and the like.

Pharmaceutically-suitable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, 2-propanol, or acetonitrile are preferred. Lists of suitable salts are found in *Remington's Pharmaceutical Sciences*, 17th Ed., Mack Publishing Company, Easton, Pa., 1985, p. 1418, the disclosure of which is hereby incorporated by reference in its entirety.

Synthesis

The compounds of the present invention may be synthesized using the general synthetic procedures described below. Each of the references cited below are hereby incorporated herein by reference.

Compounds of the Formula (I) where X is C; n is 1; m is 0; $R^2$, $R^3$, and $R^5$ are H; $R^1$ is $CO_2H$, $SO_2H$, $SO_3H$, and $PO_3H_2$; and $R^4$ is as defined above may be prepared by the following methods. When $R^4$ is $(CH_2)_pNH_2$, it may be reacted in the presence of a base and solvent under standard conditions with a halide, acid anhydride, or sulfonyl halide to produce the corresponding amide or sulfonamide derivatives. Useful bases for this procedure include pyridine, triethylamine, diethylamine, or sodium bicarbonate. Useful solvents include methylene chloride, diethyl ether, methanol, ethanol, benzene, and water. Thioamides of the amides produced above may be prepared under standard conditions using phosphorus pentasulfide in benzene. In the case where $R^1$ is tetrazole, n is 0, and $R^4$ is $NHCOCH_3$, conversion of the cyano derivative using sodium azide in dimethylformamide affords the tetrazole derivative.

Compounds of the Formula (I) where X is C; n is 1, m is 0; $R^2$ and $R^3$ are H; $R^4$ is $(CH_2)_pNHR^7$ and $R^5$ is as defined above may be prepared according to Scheme I. Compound (1) may be mono-nitrated by treatment with fuming nitric acid or other standard methods to give compound (2). The nitro group may be reduced to the amine (3) by hydrogen in the presence of 10% palladium on carbon or platinum oxide. Alternatively, the nitro group in (2) may be reduced with tin chloride or iron chloride in such solvents as ethanol, methanol, benzene, or toluene. Compound (3) may be treated with cyanogen bromide to give (4) or with sodium dicyanamide to give (7). Compound (4) can also be reacted with hydroxylamine hydrochloride to give the hydroxyguanidine adduct (6). The amine (3) may be reacted with cyanamide, $NH_2C(=NH)SO_3H$, or pyrazole carboxamidine in methanol, ethanol, or tetrahydrofuran, respectively, to yield the guanadinium derivative (5). (See G. Wagner, H. Vieweg, and H. Kohmstedt, *Pharmazie*, 28, 293 (1973); A. E. Miller and J. J. Bischoff, *Synthesis*, 777 (1986), and M. S. Bematowicz, Y. Wu, and G. R. Matsueda, *J. Org. Chem.*, 57, 2497 (1992).) Treatment of compound (3) with ammonium isothiocyanate in methanol affords the thiourea (8, S) while treatment with sodium isocyanate yields the corresponding urea (8, O).

Compounds of the Formula (I) as defined above may be mono- or bis-functionalized according to Scheme II. Reaction of compound (1) with excess N-bromo succinimide and bromine in carbon tetrachloride containing a trace of azoisobutyronitrile yields the mono- or dibromide (9). Displacement of the bromide with copper cyanide in dimethylformamide or dimethylsulfoxide yields the cyano derivative (10). Compound (10) can be hydrolyzed with strong mineral acid to yield the amide (11) which can conveniently be transformed to the thioamide (12) with phosphorus pentasulfide in benzene. Alternatively, the cyanide (10) can be converted to the amidine derivative (13) by the addition of ammonia in ethanol.

Compounds of the Formula (I) where $R^5$ is $C(R)(=N)NHC(=NH)NH_2$, $CH=NOH$ or $C(R)(=N)C(=NH)NH_2$ may be prepared according to Scheme III. Reaction of (14) with chlorine and dithiane in the presence of sodium methoxide yields the rearrangement product (15). Treatment of (15) with an acyl chloride or acid anhydride yields the N-acyl derivative (16). Removal of the dithiane protecting group is accomplished by treatment with mercuric oxide in the presence of boron trifluoride etherate in a mixture of tetrahydrofuran and water which yields the aldehyde (17). Compound (17) is then condensed with guanidine to form the guanidine derivative (19), condensed with hydroxylamine to form the oxime (18), or condensed with aminoguanidine to yield the iminoguanidine derivative (20). These reactions can be performed in water or ethanol.

For compounds of the Formula (I) where $R^5$ is $(CH(R^3)_n)_mCH_2R^3$, homologation reactions may be performed on compound (14). One-carbon homologation can be effected on (14) through the Gassman reaction [Gassman, P. G.; Drews, H. R. J. Am. Chem. Soc. 1978, 100, 7600–7610] to yield an aldehyde such as (17). The aldehyde function can be reduced to the alcohol under standard conditions using sodium borohydride in methanol. Treatment of the alcohol with phosphorus tribromide affords the benzyl bromide while further treatment with potassium cyanide in the presence of 18-crown-6 yields a benzyl cyanide. Alternatively, the aldehyde (17) can be converted to the corresponding benzyl amine by treatment with hydroxylamine hydrochloride followed by reduction of the intermediate oxime (18) with hydrogen over 10% palladium on carbon in ethanol.

A two-carbon homologation of (14) may be performed by reduction of the benzyl cyanide above with hydrogen in the presence of 10% palladium on carbon to yield the phenethylamine derivative. Alternatively, two-carbon homologations could be performed on a compound of Formula (I) where $R^1$ is $CO_2R$, n is 0, and $R^4$ is $NH_2$ with all other positions on the aromatic ring being hydrogen as shown in Scheme IV. Treatment of compound (21) with acetonitrile, boron trichloride, and aluminum chloride yielded the corresponding substituted acetophenone (22). N-acylation of (22) with acetic anhydride in pyridine followed by bromination with N-bromosuccinimide yielded the bromoketone (23). Displacement of the bromide with hexamethylenetetramine (HMTA) followed by reduction of the ketone afforded the amino alcohol (24).

Two-carbon homologations may also be performed according to Scheme V. Treatment of (25) with ethylene in the presence of palladium acetate in toluene afforded the vinyl derivative (26). Catalytic osmylation of (26) with osmium tetroxide affords the racemic diol (27). Treatment of (27) with triflic anhydride or mesylchloride affords the intermediate epoxide. Treatment of this epoxide with sodium cyanide in dimethylsulfoxide yields the compound (28). Alternatively, treatment of the epoxide with sodium azide followed by reduction with hydrogen over 10% palladium on carbon yielded the amine (24).

Three-carbon homologation is also possible via palladium-assisted allylation as described in Scheme VI. Treatment of (25) with allyl iodide in the presence of palladium acetate in toluene afforded the allyl derivative (29). Catalytic osmylation of (29) with osmium tetroxide yielded the diol (30). Triol (32) may be prepared according to Scheme VII. Treatment of (25) with palladium acetate and acrolein diethyl acetal yielded (31). Reduction of the aldehyde with sodium borohydride in methanol followed by catalytic osmylation afforded a diastereomeric mixture of triols (32). The primary alcohol of (32) may be converted to an amino group or cyano group as previously described.

A fourth substituent may be added onto a trisubstituted compound (33) by reaction with fuming nitric acid as shown in Scheme VIII to give (34). The nitro group can then be reduced by methods previously described to yield the amine (35). One-carbon homologation of the amine may be performed by starting with the appropriately-substituted dialkylmethylbenzoate by methods previously described.

Compounds of the type where $R^4=C(O)NHR^8$ can be readily prepared by the methods described in Scheme IX. Treatment of (36), which can be purchased, with oxalyl chloride followed by a primary aliphatic amine gives intermediates (37). Basic hydrolysis selectively cleaves the ester function to give the acids (38). The preparations of trisubstituted analogues is described in Scheme X. Purchased compound (39) can be selectively esterified by literature procedures to give (40). Treatment of (40) with thionylchloride followed by a primary aliphatic amine gives the amide (41). Reduction of the nitro substituent gives the amines (42). The amino group can be converted to a guanidino substituent by treatment of (42) with cyanamide to give (43). Hydrolysis of the esters of (43) under basic conditions give the acid (44).

Compound (42) can be hydrolyzed to give the acid (45) or it can be reacted with cyanogen bromide to give the intermediate (46). This intermediate can be converted to the hydroxyguanidino derivative (47) with hydroxylamine or converted to the cyanoguanidino derivative (49) with dicyanamide. Hydrolysis of (47) and (49) gives the acids (48) and (50), respectively.

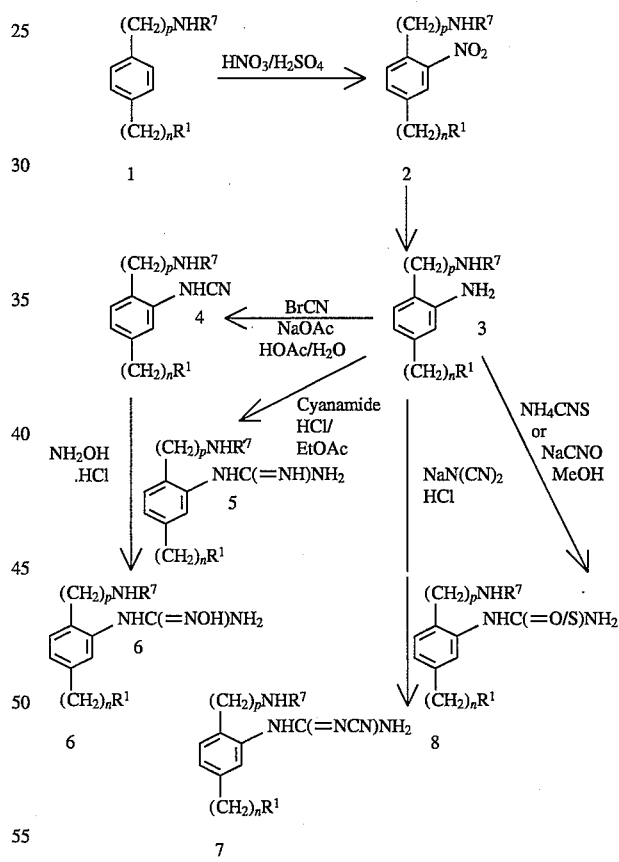

Scheme I

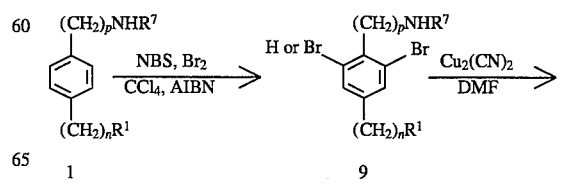

Scheme II

Scheme II (continued)
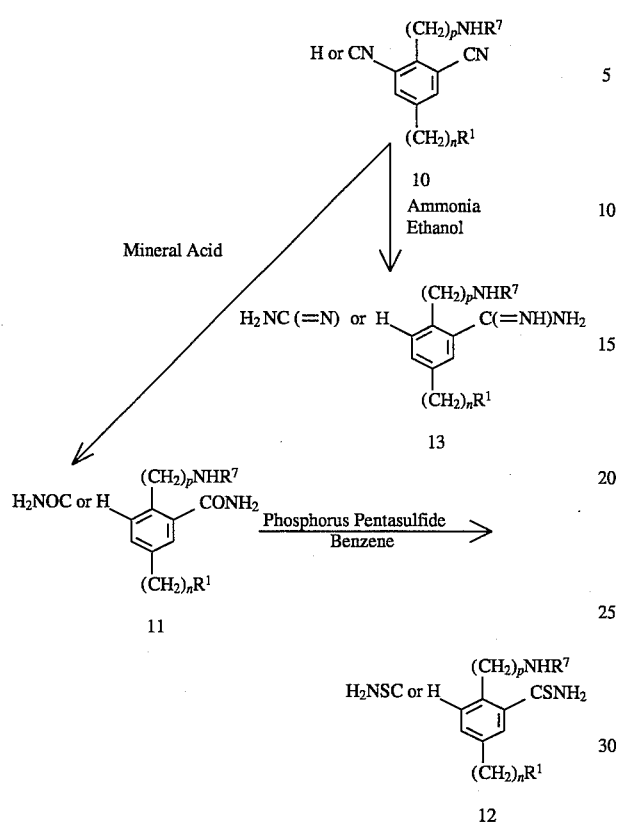
Scheme IV
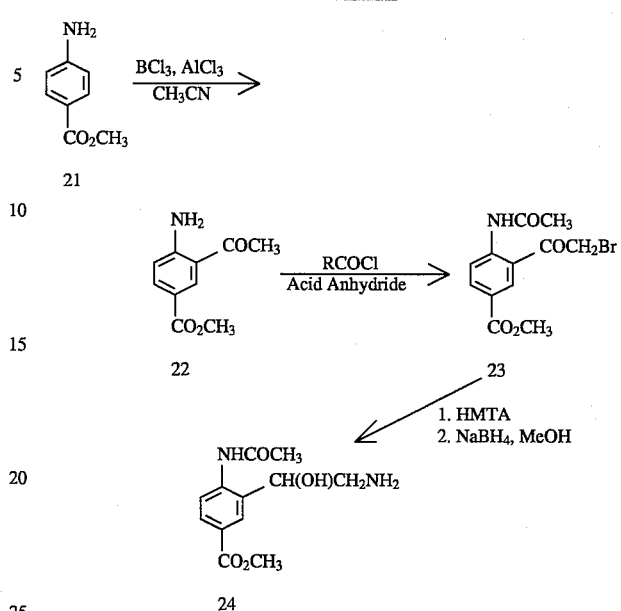
Scheme III
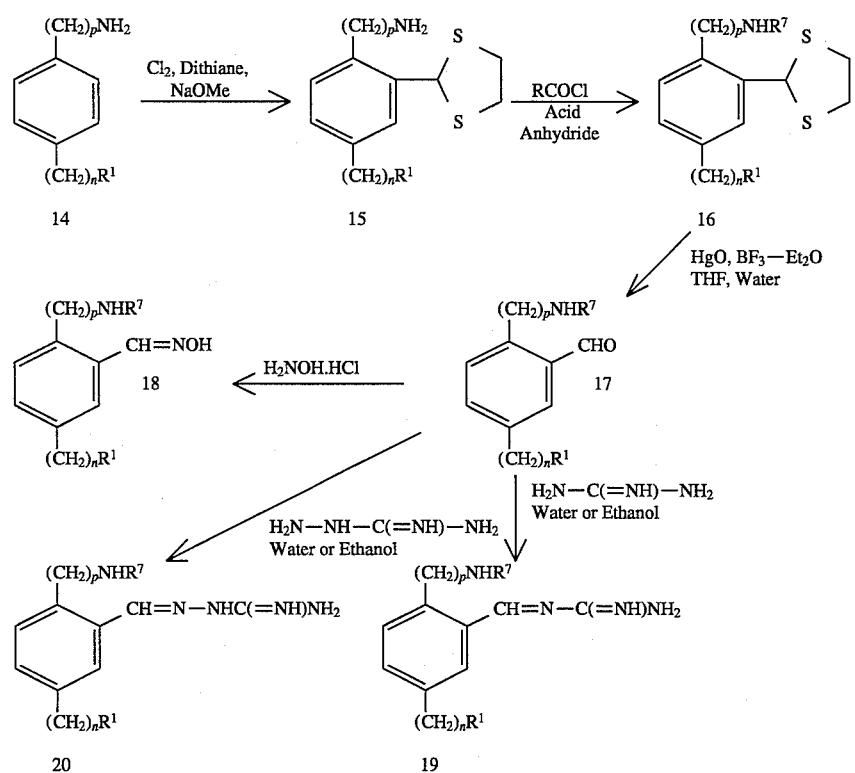

Scheme V
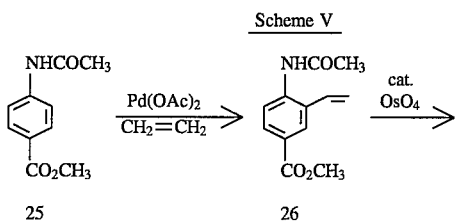
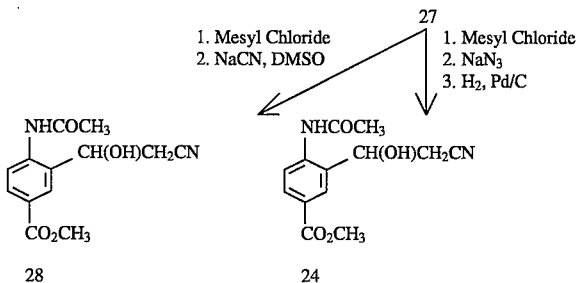
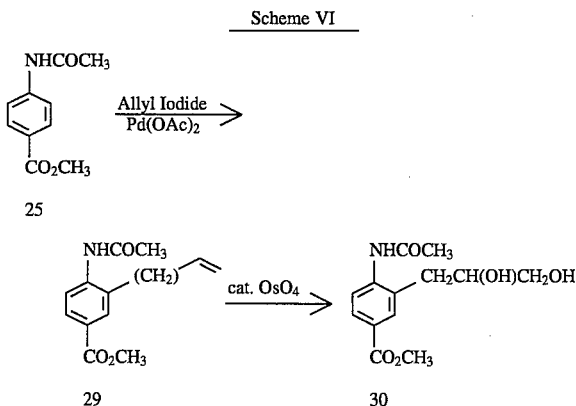
Scheme VI
Scheme VII
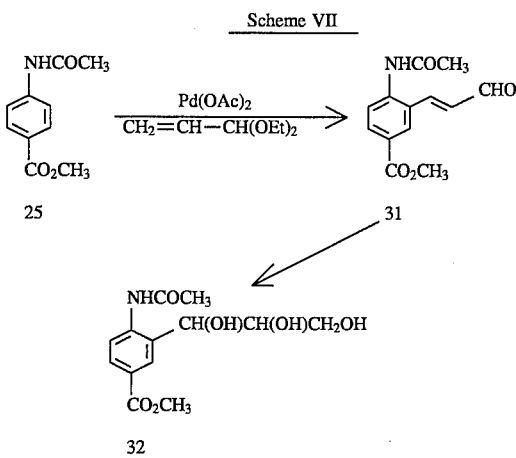
Scheme VIII
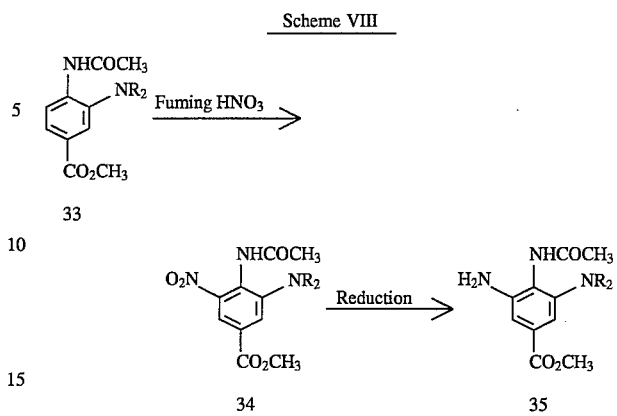
Scheme IX
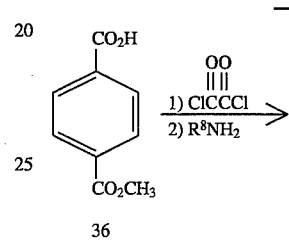
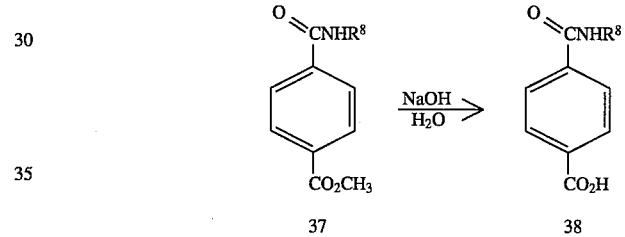
Scheme X
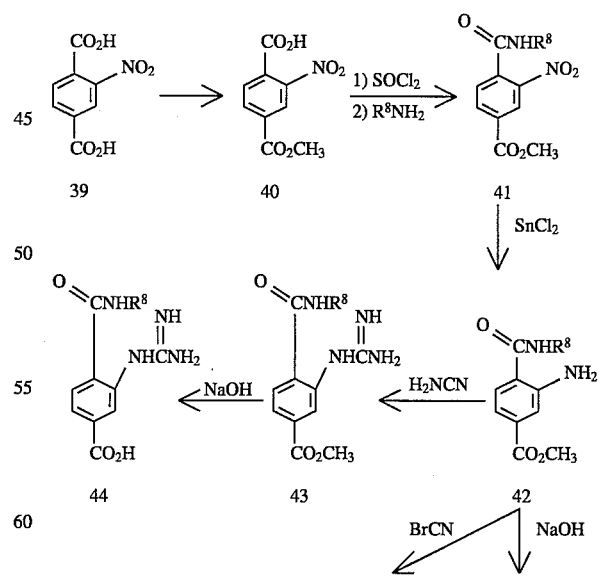

13
-continued
Scheme X

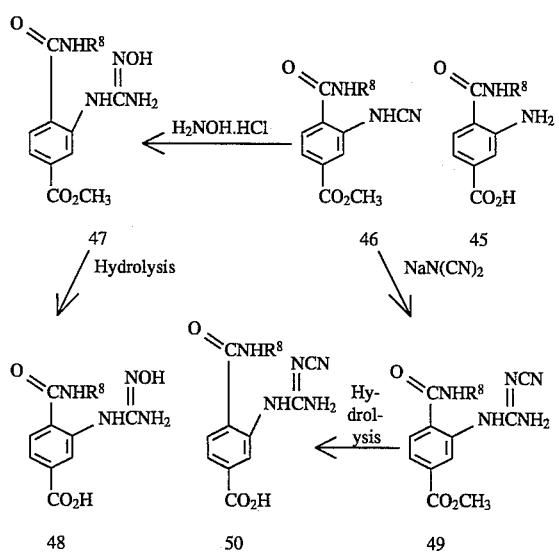

EXAMPLE 1

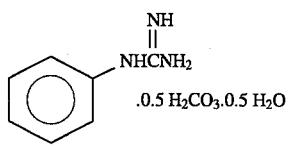

Phenylguanidine carbonate hydrate (2:1:1).

A 5-g sample of phenylguanidine carbonate was obtained from Parish Chemical Company and submitted as a white solid, mp 136°–142° C. (dec, depends upon rate of heating).

Analysis: Calculated for $C_7H_9N_3 \cdot 0.5\ H_2CO_3 \cdot 0.5\ H_2O$ (175.19): C, 51.42; H, 6.33; N, 23.99 Found: C, 51.04; H, 6.26; N, 23.99

EXAMPLE 2

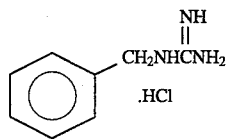

Benzylguanidine hydrochloride.

A 0.1-g sample of benzylguanidine, mp 171°–173° C., was purchased from Maybridge Chemical Company via Ryan Chemical Company, as a white crystalline solid.

Analysis: Calculated for $C_8H_{11}N_3 \cdot HCl$ (185.65): C, 51.75; H, 6.52; N, 22.63 Found: C, 51.78; H, 6.56; N, 22.61

EXAMPLE 3

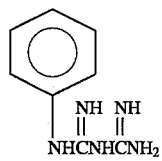

14

1-Phenylbiguanide.

A sample of 1-phenylbiguanide, mp 139°–140° C., was purchased from Research Biochemical International and submitted.

Analysis: Calculated for $C_8H_{11}N_5$: C, 54.22; H, 6.26; N, 39.52 Found: C, 54.18; H, 6.26; N, 39.47

EXAMPLE 4

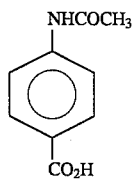

4-Acetylaminobenzoic acid.

A mixture of 4-aminobenzoic acid (Aldrich, 50.0 g, 0.365 mol) and anhydrous sodium acetate (35.0 g, 0.427 mol) in glacial acetic acid (150 mL) was heated to reflux for 15 h. The mixture was poured into cold water (1 L). The precipitate was separated by filtration and washed several times with cold water. The cake was dried in oven at 70° C. and recrystallized from 2:1 water:ethanol to give 43.0 g (68%) of the title compound as off-white flakes, mp 258° C.

Analysis: Calculated for $C_9H_9NO_3$: C, 60.32; H, 5.06; N, 7.82 Found: C, 60.51; H, 5.14; N, 7.81

EXAMPLE 5

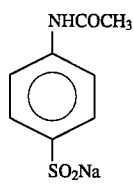

4-Acetylaminobenzenesulfinic acid, sodium salt hydrate (1:1:2).

A 25-g sample of p-acetylaminobenzenesulfinic acid sodium salt dihydrate was purchased from TCI America as a white solid, mp 313°–316° C., and was submitted.

Analysis: Calculated for $C_8H_8NO_3S \cdot Na \cdot 2\ H_2O$ (257.24): C, 37.35; H, 4.70; N, 5.46 Found: C, 37.24; H, 4.68; N, 5.37

EXAMPLE 6

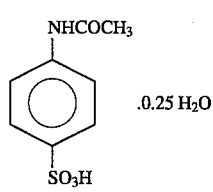

4-Acetylaminobenzenesulfonic acid hydrate (4:1).[1]

[1] Hoffmann, K. F.; Simchen, G. *Liebigs Ann. Chem.*, 282–297 (1982).

Acetanilide (Aldrich, 6.75 g, 50 mmol) was suspended in 20 mL of anhydrous 1,2-dichloroethane and cooled to 0°–5° C. Trimethylchlorosulfonate was added dropwise in about 10 min and the resulting mixture was stirred at room temperature for 30 min followed by 1 h at 50° C. The volatiles were evaporated on a rotoevaporator and the residue was diluted with 70 mL of anhydrous acetone. The brown solution was stirred at room temperature for 2 h and the precipitate collected through filtration, washed with 15 mL of acetone, dried in a pistol at acetone reflux in vacuo to give the title compound as a mauve solid (1.65 g, 15%), mp 235°–238° C.

Analysis: Calculated for $C_8H_9NO_4S \cdot 0.25\, H_2O$: C, 43.72; H, 4.35; N, 6.37 Found: C, 43.48; H, 4.51; N, 6.26

EXAMPLE 7

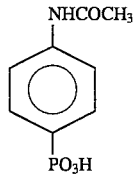

4-Acetylaminophenylphosphonic acid.

To a suspension of (4-aminophenyl)phosphonic acid (Aldrich, 0.00058 mol) in water (1.5 mL) was added sufficient sodium bicarbonate to make a clear solution. To the mixture, acetic anhydride (0.2 mL, 0.002 mol) was added and stirred for 0.5 h. Again, acetic anhydride (0.2 mL, 0.002 mol) was added and stirred for 0.5 h. The mixture was let stand at room temperature for 2 h and then concentrated hydrochloric acid (0.5 mL) was added. Fine white needles separated out which were collected by filtration, washed with water and dried to give 0.048 g (38.5%) of the title compound, mp 228° C. (rep. mp 229° C.—Bauer, H. *J. Am. Chem. Soc.* 1947, 63, 2137–2138).

Analysis: Calculated for $C_8H_{10}NO_4P \cdot H_2O$: C, 41.21; H, 5.19; N, 6.01 Found: C, 41.26; H, 5.24; N, 5.98

EXAMPLE 8

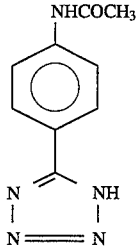

5-[4-(Acetylamino)phenyl]-1[H]-tetrazole.

A 10.0-g (0.062 mol) sample of 4-cyanoacetanilide (Aldrich), sodium azide (4.6 g, 0.07 mol), and ammonium chloride (3.75 g, 0.07 mol) were added to 100 mL of dimethylformamide in a 250-mL round-bottom flask with vigorous stirring. The mixture was stirred for 20 h at 120° C. and was then poured into 800 mL of ice water with vigorous stirring. The solid precipitate was collected by filtration and was added to 200 mL water in a 500-mL Erlenmeyer flask with vigorous stirring. The solid was again collected and dried in vacuo to give 3.4 g (27%) of the pure title compound as a white solid, mp 287° C.

Analysis: Calculated for $C_9H_9N_5O$ (203.20): C, 53.20; H, 4.46; N, 34.46 Found: C, 53.33; H, 4.54; N, 34.44

EXAMPLE 9

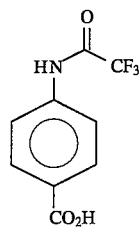

4-(Trifluoroacetamido)benzoic acid.

To a 500-mL round-bottom flask (argon atmosphere) equipped with a dropping funnel and calcium chloride drying tube were added 220 mL anhydrous pyridine, 4-aminobenzoic acid (Aldrich, 5 g, 0.036 mol), and triethylamine (7.5 g, 0.072 mol). The solution was cooled on ice and trifluoracetic anhydride was added over 45 min. The yellow solution was removed from the ice and allowed to come to room temperature with stirring. The volume was reduced in vacuo by ~60% and the solution was acidified with 3N HCl. A red solid was removed by filtration. The yellow solution was extracted with ethyl acetate three times with a total volume of ~600 mL. The organic phase was washed with 5% HCl (×5), water (×3), brine, and dried with magnesium sulfate. The drying agent was removed by filtration and the filtrate concentrated to a tan solid. This solid was recrystallized from ethyl acetate to give an off-white solid. This solid was dissolved in a minimum of ethyl acetate and applied to a flash/filtration TLC grade silica gel (~125 g) column which had been previously eluted with dichloromethane. The column was eluted with 20% ethyl acetate in dichloromethane (DCM) until TLC (5% methanol/DCM) indicated the absence of impurities (1.5 L). The product was then eluted with ethyl acetate. The solvent was again concentrated to an off-white solid which, after drying in vacuo, was recrystallized from THF/DCM (1:8 respectively). This recrystallization was repeated and activated carbon was added just before the hot filtration step. The off-white solid was collected on a filter and dried in vacuo to give 1.5 g (18%) of the title compound, mp 277°–278° C.

Analysis: Calculated for $C_9H_6F_3NO_3$ (233.145): C, 46.37; H, 2.59; N, 6.01 Found: C, 46.46; H, 2.64; N, 6.00

EXAMPLE 10

4-Thioacetamidobenzoic acid.[1]

[1] Nishiguchi; Iwakura. *J. Org. Chem.* 35, 1591–1593 (1970).

To a solution of thioacetylthioglycolic acid[2] (1.5 g, 0.010 mol), sodium hydroxide (0.4 g, 0.010 mol), and water (10 mL) was added a suspension of p-aminobenzoic acid (1.35 g, 0.010 mol) in water (10 mL). The reaction was stirred for 1 h at room temperature but did not go into solution. Additional 1N NaOH (~1.0 mL, 0.001 mol) was added until everything went into solution and the reaction was stirred for 1 h more. The reaction was then acidified with 1N HCl and the precipitate which formed was collected by filtration and washed with cold water. The product was air-dried and gave 0.85 g (44%) of the title compound as a yellow solid. The material was recrystallized from ethanol:water (1:1) and the crystals collected by vacuum filtration and dried in vacuo at acetone reflux to give the title compound as tan flakes, mp 220° C. (lit[1] mp 291° C.).

[2]Jensen; Pederson. *Acta Chemica Scandinava* 15, 1087–1096 (1961).

Analysis: Calculated for $C_9H_9NO_2S$: C, 55.36; H, 4.64; N, 7.17 Found: C, 55.23; H, 4.64; N, 7.08

EXAMPLE 11

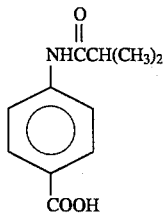

4-(2-Methylpropionylamino)benzoic acid.[1]

[1]CA 112(13) 118467s PATENT:Austria; AT 388913 B DATE:890925

A sample of ethyl 4-(2-methylpropionylamino)benzoate[2] (100 g, 0.0043 mol) was suspended in 1N NaOH (8.50 mL, 0.0085 mol). After stirring for 24 h at room temperature, the reaction was heated at 50° C. for 2 h. Thin-layer chromatographic analysis (SiO$_2$, 1:1 ethyl acetate-hexane) indicated that starting material had reacted to form a new, lower-running spot ($R_f$=0.1). The pH was adjusted to 7.0 with 1N HCl causing a white precipitate to form. The material was collected by filtration and recrystallized from methanol-ether. The residue was collected by filtration and dried in vacuo at acetone reflux to give 0.44 g (50%) of the title compound as a white solid, mp 238°–239° C.

[2]CA: 114(11) 101280u Vagaonescu, Marisa, N-Acyl Derivatives of Anesthesin. *Stud Univ. Banes-Bolyai, Chem.* 1989, 34, 12–14.

Analysis: Calculated for $C_{11}H_{13}NO_3$: C, 63.77; H, 6.28; N, 6.76 Found: C, 63.50; H, 6.40; N, 6.79

EXAMPLE 12

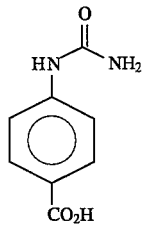

4-(1-Ureido)benzoic acid.

Urea (17.5 g, 0.292 mol), 4-aminobenzoic acid (Aldrich, 10 g, 0.073 mol), 6 mL glacial acetic acid, and 6 mL concentrated hydrochloric acid were added to 30 mL of water in a 250-mL round-bottom flask. The mixture was heated to reflux for 45 min and was then cooled. The off-white solid was removed by filtration and was washed with water twice and air dried. The pink solid was powdered and dissolved in 500 mL boiling 1:1 ethanol:THF in a 1-L Erlenmeyer flask. The solution was filtered while hot and was again boiled to reduce the volume to 200 mL. Cooling to room temperature produced an off-white solid which was removed by filtration and washed with ethanol. This solid was dried in vacuo to give 3.2 g (25%) of the title compound, mp>400° C.

Analysis: Calculated for $C_8H_8N_2O_3$ (180.162): C, 53.33; H, 4.47; N, 15.55 Found: C, 53.42; H, 4.52; N, 15.35

EXAMPLE 13

4-(Methylaminocarbonylamino)benzoic acid.

A mixture of 3.0 g (0.22 mol) of 4-aminobenzoic acid (Aldrich) in 100 mL of chloroform was treated with 10 g (0.175 mol) of methylisocyanate (Aldrich), and the mixture was stirred at ambient temperatures for three days. The mixture was concentrated and the residue was triturated with diethyl ether/petroleum ether. The solid was collected by filtration, air-dried, and then slurried with 100 mL of water. The solid was collected by vacuum filtration and the cake was sucked dry. The cake was then recrystallized from acetonitrile/water to yield 1.8 g (43%) of the title compound as a fluffy white solid, mp>400° C. (lit[1] mp>300° C.).

[1]Johnston, T. P.; McCaleb, G. S.; Montgomery, J. A. *J. Med. Chem.* 6, 669 (1963).

Analysis: Calculated for $C_9H_{10}N_2O_3$ (194.19): C, 55.66; H, 5.19; N, 14.43 Found: C, 55.76; H, 5.18; N, 14.44

EXAMPLE 14

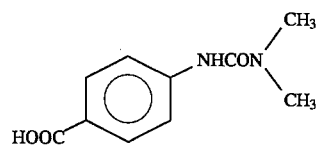

4-N,N-Dimethylcarbamyl)aminobenzoic acid.

Methyl 4-aminobenzoate (Aldrich, 5.0 g, 33 mmol) was dissolved in 120 mL of anhydrous methylene chloride containing pyridine (3.2 mL, 39.6 mmol), and dimethylaminopyridine (DMAP, 500 mg) was added. To the ice-cooled mixture was added dimethylcarbamyl chloride (3.34 mL, 36.3 mmol) while stirring. The stirring was continued for 16 h at room temperature. The reaction was quenched with water (50 mL) and the organic layer separated. The aqueous layer was extracted with chloroform (50 mL). The combined organic extract was dried over sodium sulfate. The volatiles were evaporated on a rotoevaporator to give a residue, which was applied to a column of silica gel (2 cm dia, 16.5 cm high, 42 g). Chloroform (1.2 L) eluted the starting material (3 g) while the desired material was washed with 1% methanol in chloroform (700 mL) and crystallized from chloroform-methanol-hexane. The white solid was separated, dried in air followed by drying in a pistol at acetone reflux in vacuo to give 885 mg (30% based on starting material consumed) of methyl 4-(N,N-dimethylcarbamyl)aminobenzoate, mp 169°–170° C.

Analysis: Calculated for $C_{11}H_{14}N_2O_3$: C, 59.44; H, 6.34; N, 12.60 Found: C, 59.42; H, 6.34; N, 12.55

To a suspension of methyl 4-(N,N-dimethylcarbamyl)aminobenzoate (475 mg, 2.13 mmol) in 5 mL of deionized water was added 1N sodium hydroxide (2.5 mL, aqueous) and the mixture was heated to reflux for 4 h. The reaction mixture was filtered and the filtrate was neutralized with 6N HCl. The precipitated solid was separated through filtration, crystallized from methanol-water, dried in air followed by drying in a pistol at acetone reflux in vacuo to give 246 mg (55.5%) of the title compound as a white solid, mp 237°–239° C.

EXAMPLE 15

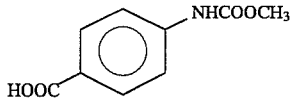

4-(Methoxycarbonyl)aminobenzoic acid.

Methyl 4-aminobenzoate (Aldrich, 5.0 g, 33 mmol) was dissolved in 120 mL of anhydrous methylene chloride containing pyridine (3.2 mL, 39.6 mmol) and dimethylaminopyridine (DMAP, 500 mg) was added. To the ice-cooled mixture was added methyl chloroformate (2.80 mL, 36.3 mmol) while stirring. The stirring was continued for 16 h at room temperature. The reaction was quenched with water (50 mL) and the organic layer separated. The aqueous layer was extracted with chloroform (50 mL). The combined organic extract was dried over sodium sulfate. The volatiles were evaporated on a rotoevaporator to give a residue, which was crystallized from chloroform-methanol. The white solid was separated, dried in air followed by drying in a pistol at acetone reflux in vacuo to give 4.95 g (71.7%) of methyl 4-(methoxycarbonyl)aminobenzoate, mp 177°–178° C.

Analysis: Calculated for $C_{10}H_{11}NO_4$: C, 57.41; H, 5.30; N, 6.69 Found: C, 57.16; H, 5.28; N, 6.64

To a suspension of methyl 4-(methoxycarbonyl)aminobenzoate (1.5 g, 7.17 mmol) in 10 mL of deionized water was added 1N sodium hydroxide (7 mL, aqueous) and the mixture was heated to 60°–70° C. for 8 h. The reaction mixture was filtered and the filtrate was neutralized with 6N HCl. The precipitated solid was separated through filtration, dried in air followed by drying in a pistol at acetone reflux in vacuo to give 754 mg (54%) of the title compound as a white solid, mp 195°–196° C.

Analysis: Calculated for $C_{10}H_9NO_5 \cdot 0.25\ H_2O$: C, 55.38; H, 4.64; N, 7.17 Found: C, 55.35; H, 4.67; N, 7.16

EXAMPLE 16

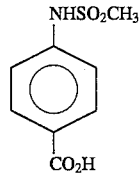

4-[(Methylsulfonyl)amino]benzoic acid.

A mixture of ethyl 4-[(methylsulfonyl)amino]benzoate (Lumma, W. C. et al. *J. Med. Chem.* 1987, 30, 758–763) (2.43 g, 0.01 mol) in 1N sodium hydroxide (22 mL, 0.022 mol) was stirred at room temperature for 24 h and then at 48° C. for 24 h. The mixture was acidified with concentrated hydrochloric acid to give a white precipitate which was separated by filtration. The cake was washed with water, dried, and recrystallized with ethanol-water to give 1.4 g (65%) of the title compound as white flakes, mp 248° C.

Analysis: Calculated for $C_8H_9NO_4S$: C, 44.64; H, 4.21; N, 6.50 Found: C, 44.71; H, 4.26; N, 6.50

EXAMPLE 17

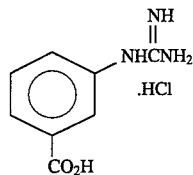

3-Guanidinobenzoic acid hydrochloride (2:1).

A mixture of 3-aminobenzoic acid (Aldrich, 2.74 g, 0.02 mol), hydrochloric acid (12N, 1.66 g, 0.02 mol), and cyanamide (1.64 g, 0.04 mol) in absolute ethanol (50 mL) was heated at reflux for 16 h. The mixture was cooled and the precipitate separated by filtration. The cake was washed several times with ether and dried under vacuum to give 1.05 g (26.6%) of the title compound as an off-white amorphous powder, mp 278° C.

Analysis: Calculated for $C_8H_9N_3O_2 \cdot 0.5\ HCl$: C, 48.67; H, 4.62; N, 21.28 Found: C, 49.10; H, 4.90; N, 21.01

EXAMPLE 18

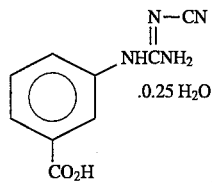

3-[Amino(cyanoimino)methyl]aminobenzoic acid hydrate (4:1).

To sodium dicyanamide in 5 mL of deionized water was added dropwise a solution of methyl 3-aminobenzoate (Aldrich, 1.30 g, 8.6 mmol) in 15 mL of 1N HCl. The resulting clear solution was heated at 80°–90° C. for 2 h. The precipitate was collected through filtration, crystallized from chloroform-methanol, dried in air followed by drying in a pistol at acetone reflux in vacuo to give 1.84 g (quantitative) of methyl 3-[amino(cyanoiminomethyl)]aminobenzoate as a white solid, mp 203°–204° C.

Analysis: Calculated for $C_{10}H_{10}N_4O_2 \cdot 0.20\ CH_3OH$: C, 54.53; H, 4.84; N, 24.94 Found: C, 54.31; H, 4.71; N, 25.30

To a suspension of methyl 3-[amino(cyanoiminomethyl)]aminobenzoate (7.3 g, 33.47 mmol) in 20 mL of deionized water was added 1N sodium hydroxide (34 mL, aqueous) and the mixture heated at reflux for 2 h. The resulting mixture was filtered and the filtrate neutralized with 6N HCl. The turbid solution was filtered and the clear filtrate further acidified using 6N HCl to pH 4.0–4.5. The white solid was separated through filtration, washed with 30 mL of water, dried in air followed by drying in a pistol at toluene reflux in vacuo to give 1.26 (18%) of the title compound, mp>300° C. Further acidification gave more solid 3.96 g (58%) which was slightly impure.

Analysis: Calculated for $C_9H_8N_4O_2 \cdot 0.25\ H_2O$: C, 51.79; H, 4.10; N, 26.84 Found: C, 51.86; H, 3.97; N, 26.66

Analysis: Calculated for $C_{10}H_{12}N_2O_3$: C, 57.67; H, 5.81; N, 13.45 Found: C, 57.65; H, 5.8 i; N, 13.44

EXAMPLE 19

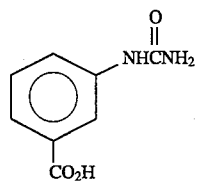

1-(3-Carboxyphenyl)urea.

Urea (17.5 g, 0.292 mol), m-aminobenzoic acid (Aldrich, 10.0 g, 0.073 mol), water (30 mL), and concentrated HCl (3 mL) were added to a 125-mL Erlenmeyer flask and boiled for 45 min. The brown suspension became a purple solution on boiling and a brown precipitate formed after 15 min. The pH of the solution was 7 after 45 min. The mixture was cooled on ice and a mauve solid was collected by filtration, slurried with water, and again collected by filtration. The solid was added to 50 mL boiling ethanol and dimethylformamide (DMF, 25 mL) was added by drop until the solid dissolved. No precipitate formed on cooling. Water was added with stirring until turbidity and then a few drops of DMF were added to give a clear solution. The solution was cooled on ice and a light-purple solid was collected by filtration. Water was added to the filtrate to precipitate a tan solid which was also collected by filtration. The tan solid was dissolved in 5% sodium bicarbonate and neutralized with a 10% solution of potassium bisulfate. The tan solid was collected by filtration, washed with water, and dried in vacuo. The tan solid was then recrystallized from 700 mL methanol and 300 mL water. After cooling, a purple solid was collected by filtration. The product was precipitated from the filtrate with the addition of 1 L of water. This light-tan solid was collected on a filter and dried in vacuo. The product was dissolved in 175 mL boiling ethanol and the volume was reduced to 75 mL and filtered while hot. This was slowly cooled to room temperature and then on ice to give an off-white solid. This solid was collected on a filter, washed with cold ethanol, and dried in vacuo to give 2.5 g (20%) of the title compound, mp 276°–280° C.

Analysis: Calculated for $C_8H_8N_2O_3$ (180.162): C, 53.33; H, 4.47; N, 15.55 Found: C, 53.55; H, 4.58; N, 15.42

EXAMPLE 20

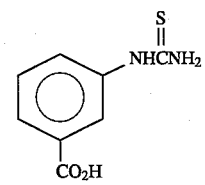

1-(3-Carboxyphenyl)-2-thiourea.

This material was purchased from Transworld Chemicals and submitted as a light-gray solid, mp 183°–185° C. It is pure by MS and $^1$H and $^{13}$C NMR.

Analysis: Calculated for $C_8H_8N_2O_2S$ (196.23): C, 48.97; H, 4.11; N, 14.28 Found: C, 48.79; H, 4.17; N, 14.22

EXAMPLE 21

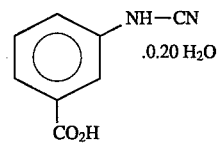

3-Cyanoaminobenzoic acid hydrate (5:1).

To a 3-aminobenzoic acid (Aldrich, 9.05 g, 66 mmol) in acetic acid:water (70 mL, 1:1) was added sodium acetate (8.12 g, 99 mmol) and the mixture was cooled in an ice-water bath. Cyanogen bromide (8.38 g, 79.2 mmol) was added in two batches in 10 min and the stirring was continued for 18 h at room temperature. The reaction mixture was poured into 350 g of an ice-water mixture with stirring. The precipitate was collected through filtration, washed with cold water (about 70 mL), dried in air, and crystallized from methanol-water. The white solid was separated through filtration, dried in air followed by drying in a pistol at toluene reflux in vacuo to give 10.40 g (95%) of the title compound, mp 238°–240° C.

Analysis: Calculated for $C_8H_6N_2O_2 \cdot 0.20\ H_2O$: C, 57.97; H, 3.89; N, 16.90 Found: C, 58.19; H, 3.87; N, 16.90

EXAMPLE 22

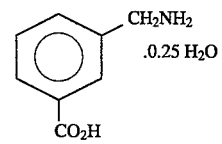

3-Aminomethylbenzoic acid hydrate (4:1).

Methyl-3-bromomethylbenzoate (5.72 g, 0.025 mol, Ryan Chemicals (Maybridge)), sodium azide (3.25 g, 0.05 mol), and tetra n-butylbromide (0.4 g, 0.00125 mol) were added to 100 mL dry benzene in a 250-mL round-bottom flask equipped with a condenser and calcium chloride drying tube in an atmosphere of argon. The mixture was then heated at reflux for 24 h and monitored by TLC (Bakerflex) using dichloromethane, 2% methanol, and 5% methanol/dichloromethane as solvents. The mixture was cooled, the inorganic salts were removed by filtration, and washed with benzene. The filtrate was added to a 250-mL separatory funnel and was then washed three times with water, once with brine, and dried with magnesium sulfate. The drying agent was removed by filtration, and the volume of the clear colorless filtrate was reduced to ~50 mL in a 100-mL round-bottom flask. The solution was saturated with argon and 3.1 g (0.025 mol) trimethylphosphite was added by drop over 10 min. The reaction bubbled during the addition (loss of nitrogen) and was mildly exothermic (once it was necessary to cool on ice with a calcium chloride drying tube in place to keep the temperature below 30° C.). The reaction was followed in the TLC system above and after 18 h, it was necessary to add ~200 mg of additional trimethylphosphite. The reaction was complete after stirring overnight. Anhydrous HCl was then bubbled into the solution with vigorous stirring. After 2 h, a precipitate formed and alter 4 h, the reaction was complete. The white solid was removed by filtration. It was then added to 200 mL ether in a 500-mL Erlenmeyer flask and vigorously stirred for 5 min. After filtration, the solid was dissolved in a minimum amount of boiling methanol and ether was added until the solution was slightly turbid. Cooling, filtering, and drying in vacuo gave 4.2 g (83%) of methyl-3-aminomethylbenzoate hydrochloride, mp 177°–178° C.

Analysis: Calculated for $C_9H_{11}NO_2 \cdot HCl \cdot 0.25\ H_2O$: C, 52.44; H, 6.10; N, 6.79 Found: C, 52.28; H, 6.02; N, 6.75

A mixture of methyl 3-aminomethylbenzoate hydrochloride (2.014 g, 0.0098 mol) in 1N sodium hydroxide (25 mL, 0.025 mol) was stirred at room temperature for 4 h. The mixture was neutralized with Dowex-H+ resin. The mixture was filtered and acetone (400 mL) was added to the filtrate. The white precipitate was collected by filtration and recrystallized from water-acetone to give 0.80 g of the title compound as a white powder, mp 278°–280° C.

Analysis: Calculated for $C_8H_9NO_2 \cdot 0.25\ H_2O$: C, 61.72; H, 6.15; N, 8.99 Found: C, 61.37; H, 6.08; N, 9.03

EXAMPLE 23

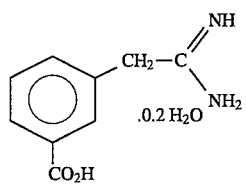

3-(2-Amino-2-imino)ethylbenzoic acid complex with water (5:1).

Methyl-3-bromomethylenebenzoate (5.0 g, 0.022 mol, Ryan Chemicals (Maybridge)), dry potassium cyanide (2.9 g, 0.044 mol), and 18-crown-6 (0.5 g, 0.0018 mol) was added to ~50 mL acetonitrile in a 100-mL round-bottom flask. The mixture was vigorously stirred for 24 h at room temperature. The reaction was monitored by TLC (Baker-flex) in dichloromethane, 2% methanol, and 5% methanol/dichloromethane. A heavy white precipitate (KBr) was removed by filtration. The filtrate was concentrated to ⅓ of the original volume and water was added until the final volume was ~100 mL. The yellow solution was added to a 250-mL separatory funnel and was extracted with dichloromethane until the organic phase was colorless and then twice more. The organic layers were combined and dried with magnesium sulfate. The drying agent was removed by filtration and the solvent was concentrated to a light yellow oil. The oil was dissolved into an equal volume of ether and was added to a 15×2.5 cm column of TLC grade silica gel and eluted with ether. The progress of the column was followed with a hand-held UV lamp. When the faster-running impurities had eluted, the product was collected and the solvent was concentrated leaving a light yellow oil. Though this oil was pure by TLC, the product was distilled (101.5° C. at 0.05 mm Hg) leaving 3.5 g (92%) of methyl-3-cyanomethylbenzoate.

Analysis: Calculated for $C_{10}H_9NO_2$: C, 68.56; H, 5.18; N, 7.99 Found: C, 68.36; H, 5.12; N, 7.97

A sample of methyl 3-(cyanomethyl)benzoate (1.87 g, 0.011 mol) was dissolved in anhydrous $CH_2Cl_2$ (100 mL) containing absolute EtOH (15 mL). The mixture was cooled to 0° C. and a stream of HCl gas passed through the solution for 10 min. The mixture was then refrigerated for 6 days. The mixture was transferred to a 500-mL flask and concentrated in vacuo (0.05 mm Hg) at 0° C. to give a white solid. The solid material was dissolved in anhydrous methanol (200 mL) and anhydrous ammonia passed through the solution for 20 min. The mixture was warmed to 50° C. for 18 h. The solution was cooled and filtered to remove solids. The filtrate was concentrated at room temperature in vacuo to give a white foam (2.5 g, quantitative). A portion (ca. 1 g) of the material was dried over toluene to give methyl 3-[(aminoiminomethyl)methyl]benzoate hydrochloride, mp 139°–140° C.

Analysis: Calculated for $C_{10}H_{12}N_2O_2 \cdot HCl$: C, 52.52; H, 5.73; N, 12.25 Found: C, 52.82; H, 5.92; N, 12.00

A mixture of methyl 3-(2-amino-2-imino)ethylbenzoate hydrochloride (0.2 g, 0.00087 mol) and ammonium hydroxide (5.0 mL) was stirred at room temperature for 24 h. The mixture was evaporated to dryness and the residue was suspended in water (5 mL). The solid was collected by filtration, washed with water, and dried under vacuum over acetone for 24 h to give 0.14 g (88%) of the title compound as a white powder, mp 219°–221° C.

Analysis: Calculated for $C_9H_{10}N_2O_2 \cdot 0.2\ H_2O$: C, 59.46; H, 5.76; N, 15.41 Found: C, 59.83; H, 5.74; N, 15.12

EXAMPLE 24

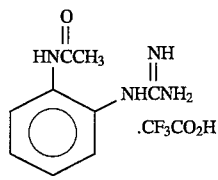

1-Acetylamino-2-[(aminoiminomethyl)amino]benzene trifluoroacetate (1:1).

Mercury(II) chloride (3.97 g, 0.0146 mol) was added to a mixture of 2-aminoacetanilide (Morgan, K. J.; Turner, A.M. *Tetrahedron* 1966, 22, 1175–1181) (2.0 g, 0.0133 mol), bis-Boc-thiourea (3.67 g, 0.0133 mol), triethylamine (6.12 mL, 0.0439 mol), and N,N-dimethylformamide (26.6 mL) at 0° C. with stirring. After 20 min at 0° C., thin-layer chromatographic analysis ($SiO_2$, ethyl acetate:hexane 1:1) showed formation of a compound with a higher $R_f$ and disappearance of the starting material. The mixture was then diluted with ethyl acetate (350 mL) and filtered through a pad of Celite. The filtrate was washed with water (75.0 mL) and brine (75.0 mL), dried over $Na_2SO_4$, and concentrated in vacuo. After column chromatography ($SiO_2$, ethyl acetate:hexane 1:1), the resulting solid was dried in vacuo to give 3.0 g (57.4%) of the title compound as a white solid, mp 165°–166° C. (ethyl acetate).

Analysis: Calculated for $C_{19}H_{28}N_4O_5$: C, 58.15; H, 7.19; N, 14.28 Found: C, 58.18; H, 7.16; N, 14.34

A sample of 1-acetylamino-2-{[t-butoxycarbonylamino-t-butoxycarbonyliminomethyl]amino}benzene (1.10 g, 0.0028 mol) in dichloromethane (10.0 mL) containing trifluoroacetic acid (0.5 mL, 0.0062 mol) was stirred 16 h at room temperature. Thin-layer chromatographic analysis ($SiO_2$, ethyl acetate:hexane 1:1) showed formation of a compound (80%) as a lower $R_f$ spot in addition to the remaining starting material (20%). The reaction contents were concentrated in vacuo. Additional trifluoroacetic acid (1.5 mL, 0.0186 mol) and dichloromethane (10.0 mL) were added to the flask and the reaction was allowed to stir for 2 h. Thin-layer chromatographic analysis ($SiO_2$, ethyl acetate:hexane 1:1) showed only one spot. MS analysis indicated the presence of a mono-Boc intermediate and the guanidino product. After concentration, trifluoroacetic acid (0.5 mL, 0.0062 mol) and dichloromethane (10.0 mL) were added to the syrup. The reaction was complete after 16 h according to thin-layer chromatographic analysis ($SiO_2$, chloroform:methanol 4:1). The contents were concentrated and the residue was triturated with dichloromethane. The resulting solid was collected by filtration and dried in vacuo to give 0.5 g (58%) of the title compound as an off-white solid, mp 160°–162° C.

Analysis: Calculated for $C_{11}H_{13}F_3N_4O_3$: C, 43.14; H, 4.28; N, 18.29 Found: C, 42.97; H, 4.21; N, 18.13

EXAMPLE 25

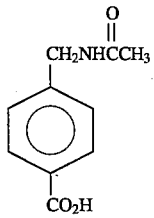

4-[(Acetylamino)methyl]-benzoic acid.

A mixture of 4-aminomethylbenzoic acid (Aldrich, 1.51 g, 0.01 mol) and anhydrous sodium acetate (1.5 g, 0.018 mol) in glacial acetic acid (5 mL) was heated at reflux for 18 h. On cooling, the mixture was poured into cold water (50 mL). The precipitate was separated by filtration and washed several times with cold water. The cake was recrystallized from water to give 1.4 g (72.5%) of the title compound as a white powder, mp 195° C.

Analysis: Calculated for $C_{10}H_{11}NO_3$: C, 62.17; H, 5.74; N, 7.25 Found: C, 62.14; H, 5.75; N, 7.20

EXAMPLE 26

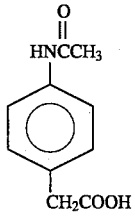

4-(Acetamido)phenylacetic acid.

To 4-aminophenylacetic acid (Aldrich, 5 g, 33 mmol) in 50 mL of anhydrous methanol was added 2.5 mL of concentrated sulfuric acid cautiously. The mixture was heated to reflux for 4 h. The reaction was cooled to room temperature and neutralized with sodium carbonate. The volatiles were evaporated on a rotoevaporator and the residue triturated with chloroform (80 mL) and saturated sodium bicarbonate (100 mL). The chloroform layer was separated and filtered through a small pack of silica gel. The solvent was evaporated and the residue purified through vacuum distillation at 130°–150° C. to give 2.7 g (50%) of methyl 4-aminophenylacetate as a light brown syrup.

Analysis: Calculated for $C_9H_{11}NO_2$: C, 65.43; H, 6.71; N, 8.47 Found: C, 65.41; H, 6.79; N, 8.42

Methyl 4-aminophenylacetate (1.0 g, 6.05 mmol) was dissolved in 5 mL of anhydrous pyridine containing dimethylaminopyridine (DMAP, 100 mg) and acetic anhydride (5 mL). The stirring was continued for 16 h at room temperature. The volatiles were evaporated on a rotoevaporator and the residue diluted with chloroform-water (50 mL, 1:1). After shaking, the chloroform layer was separated, washed with 20 mL of 1N HCl, dried over sodium sulfate, and the chloroform evaporated. The residue was crystallized from chloroform-hexane, separated through filtration, dried in air followed by drying in a pistol at acetone reflux in vacuo to give methyl (4-acetamido)phenyl acetate as an opalescent solid, 1.10 g (88%), mp 104°–106° C.

Analysis: Calculated for $C_{11}H_{13}NO_3$: C, 63.75; H, 6.32; N, 6.75 Found: C, 63.56; H, 6.34; N, 6.65

To a suspension of methyl (4-acetamido)phenyl acetate (830 mg, 4 mmol) in 2 mL of deionized water was added 1N sodium hydroxide (4 mL, aqueous) and the mixture was heated to 60°–70° C. for 3 h. The reaction mixture was filtered and the filtrate neutralized with 6N HCl. The solid was separated through filtration, dried in air followed by drying in a pistol at acetone reflux in vacuo to give 530 mg (69%) of the title compound (CAS Registry No. 18699-02-0) as a cream-colored solid, mp 158°–160° C.

Analysis: Calculated for $C_{10}H_{11}NO_3$: C, 62.21; H, 5.74; N, 7.25 Found: C, 62.30; H, 5.70; N, 7.21

EXAMPLE 27

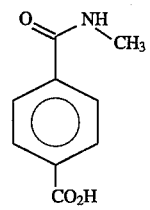

4-(Methylaminocarbonyl)benzoic acid.

Monomethylterephthalate (Aldrich, 5.0 g, 0.028 mol) was added to 80 mL of dry benzene in a 250-mL round-bottom flask under argon and fitted with a calcium chloride drying tube. Dry pyridine (4.4 g, 0.056 mol) was added and the mixture was stirred for 15 min. Oxalyl chloride (3.66 g, 0.029 mol) was added by drop over 10 min. The mixture bubbled vigorously during the addition and a heavy white precipitate formed. The mixture was vigorously stirred for 40 min and followed by TLC (three solvent systems: dichloromethane, 2% methanol, and 5% methanol). Anhydrous methylamine was bubbled into the mixture for 10 min. The precipitate dissipated somewhat and the solution color changed from colorless to green and finally to yellow. The mixture was then stirred overnight. The remaining white precipitate was collected on a filter and washed with benzene. The filtrate was washed with water and dried over sodium sulfate. The drying agent was removed by filtration, washed with benzene, and the solvent concentrated to give a white solid. The solids were combined and dissolved in 300 mL dichloromethane. The solution was washed 3 times with 5% HCl, 3×5% sodium bicarbonate, 3×water, 1×brine, and then dried over sodium sulfate. The drying agent was removed by filtration and the filtrate concentrated to give a white solid which was dried in vacuo. This white solid was recrystallized from methanol to give 2 g (37%) of methyl 4-(methylaminocarbonyl)benzoate, mp 126° C.

Analysis: Calculated for $C_{10}H_{11}NO_3$ (193.202): C, 62.17; H, 5.74; N, 7.25 Found: C, 62.16; H, 5.74: N, 7.25

Methyl 4-(methylaminocarbonyl)benzoate (1.9 g, 0.0098 mol) was added to 10 mL 1.5M NaOH (1.5 eq) and 30 mL water in a 125-mL Erlenmeyer flask. The suspension was stirred for 1 h at room temperature. The solid gradually dissolved during this time. The solution was filtered and acidified to produce a white solid. The solid was removed by filtration, washed twice with water, and dried in vacuo to give 1.60 g (90%) of the title compound, mp 270° C.

Analysis: Calculated for $C_9H_9NO_3$ (179.175): C, 60.03; H, 5.06; N, 7.82 Found: C, 60.07; H, 5.03; N, 7.77

EXAMPLE 28

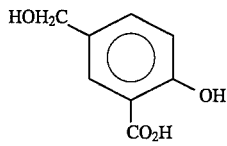

2-Hydroxy-5-(hydroxymethyl)benzoic acid.

To a solution of methyl-5-formylsalicylate (Kadaba, *J. Pharm. Sci.* 1974, 63, 1333–1335) (1.80 g, 0.01 mol) in methanol (20 mi) at 0° C. was added sodium borohydride (0.38 g, 0.01 mol) in 4 portions during 0.5 h. The solution was further stirred at 0° C. for 2 h and then at room temperature for 0.3 h. It was neutralized with hydrochloric acid and concentrated under vacuum. The residue was passed through a column of silica gel using 1:1 ethyl acetate:hexane as the eluent to give 1.0 g (55%) of methyl-2-hydroxy-5-hydroxymethylbenzoate as a pale yellow powder, mp 66°–67° C.

Analysis: Calculated for $C_9H_{10}O_4$: C, 59.34; H, 5.49 Found: C, 59.40; H, 5.58

A solution of methyl-2-hydroxy-5-(hydroxymethyl)benzoic (0.364 g, 0.002 mol) in 1N sodium hydroxide (4 mL) was stirred at room temperature for 16 h. The solution was acidified with hydrochloric acid and concentrated under vacuum. The residue was dissolved in methanol (5 mL) and filtered. The filtrate was concentrated and the residue was dissolved in water (4 mL). The resultant mixture was extracted with 10:1 ethyl acetate:methanol (5 mL). The extract was concentrated to give 0.18 g (54%) of the title compound as an off-white powder, mp 108°–110° C.

Analysis: Calculated for $C_8H_8O_4$: C, 57.14; H, 4.76 Found: C, 56.88; H, 4.76

EXAMPLE 29

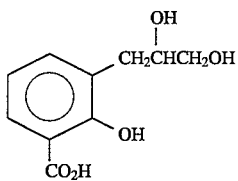

2-Hydroxy-3-(2'R,3'-dihydroxypropyl)benzoic acid.

To a solution of 1:1 water and tert-butanol (50 mL), AD-mix-α (Aldrich, 7.0 g) was added and stirred for 0.1 h. The mixture had two layers; the lower layer was yellow. To this mixture, methyl-2-hydroxy-3-allylbenzoate (Claisen, *Chem. Ber.* 1912, 45, 3157–3166) (0.96 g, 0.005 mol) was added in one portion and stirred at room temperature for 48 h. The reaction mixture was cooled to 0° C. and sodium sulphite (7.5 g) was added. The reaction was stirred at 0° C. for 0.3 h and then at room temperature for 0.5 h. It was extracted with ethyl acetate (3×50 mL), the combined organic layers were dried over sodium sulphate, filtered, and concentrated. The residue was passed through a column of silica gel first using 1:1 ethyl acetate:hexane as eluent to recover the starting material and then pure ethyl acetate to give 0.96 g (85%) of methyl-2-hydroxy-3-(2'R,3'-dihydroxypropyl)benzoate as a white powder, mp 72°–73° C.

Analysis: Calculated for $C_{11}H_{14}O_5$: C, 58.40; H, 6.19 Found: C, 58.60; H, 6.30

A solution of methyl-2-hydroxy(2'R,3'-dihydroxypropyl)benzoate (0.80 g, 0.0035 mol) in 1N sodium hydroxide (6 mL) was stirred at room temperature for 16 h. The solution was acidified with hydrochloric acid and concentrated under vacuum. The residue was washed with cold water (5 mL) and filtered. The cake was washed with cold water and then recrystallized from water to give 0.48 g (64%) of the title compound as a white powder, mp 145°–147° C.

Analysis: Calculated for $C_{10}H_{12}O_5$: C, 56.60; H, 5.66 Found: C, 56.58; H, 5.74

EXAMPLE 30

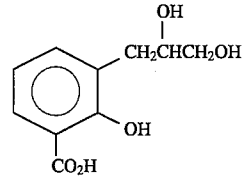

2-Hydroxy-3-(2'S,3'-dihydroxypropyl)benzoic acid.

To a solution of 1:1 water and tert-butanol (50 mL), AD-mix-β (Aldrich, 7.0 g) was added and stirred for 0.1 h. The mixture had two layers; the lower layer was yellow. To this mixture, methyl-2-hydroxy-3-allylbenzoate (Claisen, *Chem. Ber.* 1912, 45, 3157–3166) (0.96 g, 0.005 mol) was added in one portion and stirred at room temperature for 48 h. The reaction mixture was cooled to 0° C. and sodium sulphite (7.5 g) was added. The reaction was stirred at 0° C. for 0.3 h and then at room temperature for 0.5 h. It was extracted with ethyl acetate (3×50 mL), the combined organic layers were dried over sodium sulphate, filtered, and concentrated. The residue was passed through a column of silica gel first using 1:1 ethyl acetate:hexane as eluent to recover the starting material and then pure ethyl acetate to give 0.96 g (85%) of methyl-2-hydroxy-3-(2'S,3'-dihydroxypropyl)benzoate as a white powder, mp 66°–67° C.

Analysis: Calculated for $C_{11}H_{14}O_5$: C, 58.40; H, 6.19 Found: C, 58.40; H, 6.26

A solution of methyl-2-hydroxy-2'S,3'-dihydroxypropyl)benzoate (0.82 g, 0.0036 mol) in 1N sodium hydroxide (6 mL) was stirred at room temperature for 16 h. The solution was acidified with hydrochloric acid and concentrated under vacuum. The residue was washed with cold water (5 mL) and filtered. The cake was washed with cold water and then recrystallized from water to give 0.46 g (60%) of the title compound as a white powder, mp 147°–149° C.

Analysis: Calculated for $C_{10}H_{12}O_5$: C, 56.60; H, 5.66 Found: C, 56.58; H, 5.70

EXAMPLE 31

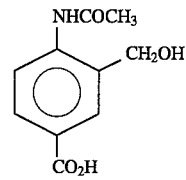

4-Acetylamino-3-hydroxymethylbenzoic acid, complex with NaOH [5:3].

Methyl-4-acetylamino-3-formylbenzoate (Gassman, P. G.; Drews, H. R. *J. Am. Chem. Soc.* 1978, 100, 7600–7610) (0.331 g, 0.0015 mol) was dissolved in methanol (5 mL) and cooled to 0° C. Sodium borohydride (0.057 g, 0.0015 mol) was added to the above solution at 0° C. and stirred for 0.25 h. The reaction was complete by TLC during this time. It was neutralized with H+ resin, filtered, and the filtrate concentrated. The residue was dried under vacuum over phosphorus pentoxide at 56° C. to give 0.33 g (99%) of methyl-4-acetylamino-3-hydroxymethylbenzoate as a pink solid, mp 60° C.

Analysis: Calculated for $C_{11}H_{13}NO_4 \cdot 0.1$ NaOH: C, 58.14; H, 5.77; N, 6.14 Found: C, 57.93; H, 5.64; N, 6.08

Methyl-4-acetylamino-3-hydroxymethylbenzoate (0.215 g, 0.001 mol) was stirred in 2 mL of water and 1 mL of 1N sodium hydroxide was added. The reaction mixture was stirred for 4 h at room temperature (complete by TLC, ethyl acetate). It was neutralized with H+ resin, filtered, and the filtrate concentrated under vacuum to give 0.2 g (100%) of the title compound as a white powder, mp 175°–180° C.

Analysis: Calculated for $C_{10}H_{11}NO_4 \cdot 0.6$ NaOH: C, 51.50; H, 4.97: N, 6.00 Found: C, 51.60; H, 4.82: N, 5.98

EXAMPLE 32

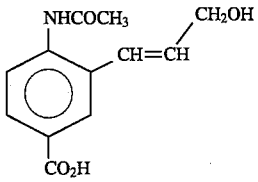

trans-4-Acetylamino-3-(2'-propen-1'-ol)benzoic acid.

A mixture of ethyl 4-acetylaminobenzoate (Coneglio, L. *Rend Acad Sci. Napoli* [3] 1931, 36, 56–60) (8.28 g, 0.04 mol) and palladium acetate (4.50 g, 0.02 mol) in dry toluene (100 mL) was heated at reflux for 2 h under nitrogen. The solution was cooled to 50° C., the toluene decanted, and the residue washed with fresh toluene. The combined filtrates were heated at reflux for 3 h, the precipitate was collected by filtration and mixed with the previous residue. The combined greenish residues were dried under vacuum for 3 h. To this residue, toluene (100 mL), acrolein diethyl acetal (17.5 g, 0.135 mol), and triethylamine (11.2 g, 0.111 mol) were added and the mixture was heated at reflux for 3 h. On cooling, the palladium was removed by filtration through Celite and the filtrate was concentrated. The residue was passed through a column of silica gel using 1:1 ethyl acetate:hexane as eluent to give 1.1 g (20.8%) of ethyl 4-acetylamino-3-[3'-(2'-propen-1'-al)]benzoate as an off-white flocculent solid, mp 171° C.

Analysis: Calculated for $C_{14}H_{15}NO_4 \cdot 0.2$ $H_2O$: C, 63.48; H, 5.86: N, 5.29 Found: C, 63.61; H, 5.88: N, 5.22

A mixture of ethyl 4-acetylamino-3-(3'-(2'-propen-1'-al)]benzoate (0.522 g, 0.002 mol) in methanol (20 mL) was cooled to 0° C. To this mixture, sodium borohydride (0.091 g, 0.0024 mol) in methanol (2 mL) was added and the mixture stirred for 0.25 h. The mixture was neutralized with H+ resin (Dowex-50W) and filtered. The filtrate was concentrated and the residue passed through a column of silica gel using 19:1 chloroform:methanol as eluent to give 0.410 g (76%) of ethyl 4-acetylamino-3-[3'-(2'-propen-1'-ol)]benzoate as a pale yellow powder, mp 118°–119° C.

Analysis: Calculated for $C_{14}H_{17}NO_4 \cdot 0.5$ $H_2O$: C, 61.75; H, 6.66; N, 5.15 Found: C, 61.68; H, 6.38; N, 5.12

A mixture of trans-ethyl 4-acetylamino-3-(2'-propen-1'-ol)benzoate (0.272 g, 0.001 mol) in 0.5N sodium hydroxide (5 mL, 0.0025 mol) was stirred at room temperature for 8 h. The mixture was neutralized with H+ resin and quickly filtered. The filtrate on cooling gave pale yellow crystals. The crystals were separated by filtration and washed with cold water to give 0.065 g (28%) of the title compound, mp 214°–215° C. The filtrate on acidification with hydrochloric acid gave a pink precipitate. The pink solid was separated by filtration and washed with cold water to give 0.130 g (56%, second crop) of the title compound, mp 207°–208° C.

Analysis: Calculated for $C_{12}H_{13}NO_4$: C, 61.27; H, 5.57; N, 5.95 Found: C, 61.12; H, 5.62; N, 5.88

EXAMPLE 33

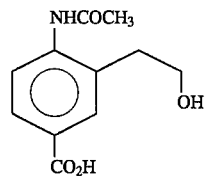

β-(2-N-Acetylamino-5-carboxyphenyl)ethanol.

To a mixture of methyl 4-aminobenzoate (Aldrich, 15.1 g, 0.1 mol) in methylene chloride (400 mL) at −70° C. was added a solution of t-butyl hypochlorite (12.0 g, 0.011 mol in 50 mL methylene chloride) over a period of 10 min. The mixture was stirred at −70° C. for further 10 min and ethyl methylthioacetate (13.42 g, 0.1 mol in 50 mL methylene chloride) was added to it over a period of 10 min. The mixture was further stirred for 1 h at the same temperature and subsequently, triethylamine (11.2 g, 0.11 mol in 40 mL methylene chloride) was added to it over a period of 10 min. The cooling bath was removed and the mixture was brought to room temperature. Water (120 mL) was added, the organic layer separated, dried over sodium sulphate, filtered, and concentrated to give a brown viscous oil. The oil was taken in ether (200 mL) and triethylamine (40 mL) and cooled to 0°–5° C. in an ice bath. Acetyl chloride (8.6 g, 0.11 mol) in ether (50 mL) was added dropwise over a period of 15 min. The reaction mixture was stirred for 1 h. Water (200 mL) was added, the organic layer separated, washed with water, dried over sodium sulphate, filtered, and concentrated to give a syrup. This syrup was purified by passing through a column of silica gel using ethyl acetate:hexane (1:2) as eluent. The appropriate fractions were pooled, combined, and concentrated. The residue of the desired product was recrystallized from ethyl acetate-hexane to give 9.5 g (29.3%) of ethyl α-(2-acetylamino-5-methoxycarbonylphenyl)-α-methylthio acetate as a white solid, mp 95°–96° C.

Analysis: Calculated for $C_{15}H_{19}NO_5S$: C, 55.37; H, 5.88; N, 4.31 Found: C, 55.43; H, 5.91; N, 4.28

To a mixture of ethyl α-(2-acetylamino-5-methoxycarbonylphenyl)-α-methylthio acetate (6.5 g, 0.02 mol) in tetrahydrofuran (150 mL), Raney nickel (about 20 mL slurry in tetrahydrofuran, washed several times with water and tetrahydrofuran) was added in portions over a period of 30 min. The reaction mixture was stirred for 15 min and Raney nickel was removed by filtration through Celite. The filtrate was concentrated to give a white residue which was recrystallized from ethyl acetate-hexane to give 5.2 g (93%) of ethyl α-(2-acetylamino-5-methoxycarbonylphenyl)acetate as a white solid, mp 119° C.

Analysis: Calculated for $C_{14}H_{17}NO_5$: C, 60.21; H, 6.13; N, 5.02 Found: C, 60.12; H, 6.13; N, 4.93

To a mixture of ethyl α-(2-acetylamino-5-methoxycarbonylphenyl)acetate (4.18 g, 0.015 mol) in methanol (60 mL), 1N sodium hydroxide (15.0 mL, 0.015 mol) was added over a period of 10 min. The mixture was stirred at room temperature for 1 h. After dilution with water (50 mL), the mixture was filtered and the filtrate neutralized with concentrated hydrochloric acid. The precipitate obtained was collected by filtration and washed with water. The cake was recrystallized from ethyl acetate and dried to give 2.3 g (61%) of α-(2-acetylamino-5-methoxycarbonylphenyl)acetic acid as a white solid, mp 194° C.

Analysis: Calculated for $C_{12}H_{13}NO_5$: C, 57.37; H, 5.22; N, 5.58 Found: C, 57.10; H, 5.26; N, 5.50

To a mixture of α-(2-N-acetylamino-5-methoxycarbonylphenyl)acetic acid (1 g, 4 mmol), tetrahydrofuran (10 mL), and triethylamine (0.56 mL, 4 mmol), ethyl chloroformate (0.38 mL, 4 mmol) was added over a period of 5 min at 0° C. After stirring for an additional 20 min at the same temperature, the mixture was filtered with suction, and the cake was washed with tetrahydrofuran (3×10 mL). Sodium borohydride (0.48 g, 12.6 mmol) was added to the filtrate in one portion. Then methanol (2.6 mL) was added dropwise over a period of 1 h at 10° C. After stirring for an additional 30 min, the reaction mixture was quenched carefully with 1N HCl close to pH=7. To this mixture was added water (25 mL) and ether (25 mL). The organic layer was separated and the aqueous layer extracted with methylene chloride (3×10 mL). The organic layers were combined, dried with sodium sulfate, and the solvent removed in vacuo to give 0.91 g of crude product as a white residue. The crude product was purified by flash column chromatography (75–100% ethyl acetate in hexane) to obtain β-(2-N-acetylamino-5-methoxycarbonylphenyl)ethanol [$R_f$ 0.16 in ethyl acetate:hexane (3:1)] 0.55 g (58%) as a white solid, mp 134°–136° C.

Analysis: Calculated for $C_{12}H_{15}NO_4$: C, 60.75; H, 6.37; N, 5.90 Found: C, 60.70; H, 6.37; N, 5.81

A solution of β-(2-N-acetylamino-5-methoxycarbonylphenyl)ethanol (0.71 g, 3 mmol) in 1N NaOH (6 mL) was stirred at room temperature for 1 h. The reaction mixture was filtered and the pH was adjusted between 2–3 using 1N HCl. The product obtained on standing for 1 h was collected by filtration, washed with small amounts of water and ether, and dried in a pistol at toluene reflux overnight in vacuo to furnish 0.58 g (87%) of the title compound as a light brown solid, mp 206°–208° C. (dec).

Analysis: Calculated for $C_{11}H_{13}NO_4$: C, 59.19; H, 5.87; N, 6.27 Found: C, 59.05; H, 5.88; N, 6.22

EXAMPLE 34

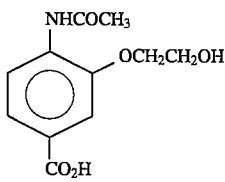

4-Acetylamino-3-(2-hydroxyethoxy)benzoic acid.

To methyl 3-hydroxy-4-nitrobenzoate (*Dictionary of Organic Compounds*, Heilbron, I.; Brunburg, H. M., Eds.; Vol. 3; 1953, Oxford University Press: New York, N.Y.; p 700) (5.0 g, 0.0254 mol) dissolved in acetone (50 mL) was added potassium carbonate (4.3 g, 0.0300 mol), sodium iodide (0.375 g, 0.0025 mol), and 2-bromoethanol (3.44 g, 0.0275 mol). After refluxing for 60 h, thin-layer chromatographic analysis ($SiO_2$, 3:2 hexane:ethyl acetate) showed partial disappearance (50%) of the starting material along with the formation (50%) of a new, lower-running spot ($R_f$=0.2). To the reaction mixture, additional potassium carbonate (4.3 g, 0.0300 mol), sodium iodide (0.375 g, 0.0025 mol), and 2-bromoethanol (3.44 g, 0.0275 mol) were added. After refluxing for 24 h more, thin-layer chromatographic analysis ($SiO_2$, 3:2 hexane:ethyl acetate) showed increased disappearance of the starting material along with the formation (70%) of a lower-running spot ($R_f$=0.2). One-half of the reaction was poured into water (200 mL) and then extracted three times with 100-mL portions of ethyl acetate. The organic layer was concentrated and the residue recrystallized from ethyl acetate-hexane. The material was collected by filtration and dried in vacuo at acetone reflux to give 0.878 g (14%) of methyl 3-(2-hydroxyethoxy)-4-nitrobenzoate as an orange solid, mp 97°–98° C.

Analysis: Calculated for $C_{10}H_{11}NO_6$: C, 49.79; H, 4.56; N, 5.81 Found: C, 49.58; H, 5.64; N, 5.78

To a sample of methyl 3-(2-hydroxyethoxy)-4-nitrobenzoate (3.28 g, 0.0136 mol) dissolved in ethanol was added platinum oxide (50 mg). The mixture was hydrogenated for 40 min at 35 psi. Thin-layer chromatographic analysis ($SiO_2$, 3:2 hexane:ethyl acetate) showed disappearance of starting material along with the formation of a new, lower-running spot ($R_f$=01) indicating the reaction was complete. The mixture was then filtered through a pad of Celite and the pad washed with fresh ethanol. The filtrate was concentrated and dried in vacuo to give 2.9 g (100%) of methyl 4-amino-3-(2-hydroxyethoxy)benzoate as an off-white solid.

To methyl 4-amino-3-(2-hydroxyethoxy)benzoate (2.98 g, 0.0141 mol) dissolved in dichloromethane (200 mL) was added acetic anhydride (1.49 mL, 0.0156 mol) and pyridine (1.34 mL, 0.0156 mol). After stirring for 3 h at room temperature, thin-layer chromatographic analysis ($SiO_2$, ethyl acetate) showed disappearance of the starting material along with the appearance of a new lower-running spot ($R_f$=03) indicating the reaction was complete. The reaction was poured into water (70 mL) and the organic layer washed three times with water (50 mL). The organic layer was concentrated and then dried in vacuo. Thin-layer chromatographic analysis ($SiO_2$, ethyl acetate) showed formation of some material as a higher-running spot ($R_f$=0.8) in addition to the product. Methanol (50 mL) and a catalytic amount of sodium methoxide was added to the residue. After 1 h, thin-layer chromatographic analysis ($SiO_2$, ethyl acetate) showed only the desired product. The solution was neutralized with H+ resin, filtered, and then concentrated. The residue was recrystallized from ethyl acetate to give 1.88 g (53%) of methyl 4-acetylamino-3-(2-hydroxyethoxy)benzoate as an off-white solid.

A sample of methyl 4-acetylamino-3-(2-hydroxyethoxy)benzoate (1.51 g, 0.0060 mol) was suspended in 1N NaOH (12.0 mL, 0.0119 mol). After stirring for 1 h, thin-layer chromatographic analysis ($SiO_2$, ethyl acetate) showed disappearance of starting material along with appearance of a new lower-running spot (Rf =0.1) indicating the reaction was complete. The reaction mixture when neutralized with concentrated HCl formed a white precipitate. The material was collected by filtration, washed with water, and then dried in vacuo at acetone reflux to give 0.47 g (34%) of the title compound as a tan solid, mp 207.5°–208.5° C.

Analysis: Calculated for $C_{11}H_{13}NO_5$: C, 55.23; H, 5.44; N, 5.86 Found: C, 55.07; H, 5.53; N, 5.87

EXAMPLE 35

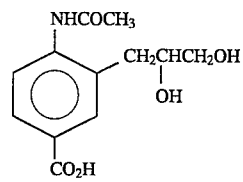

4-Acetylamino-3-(2',3'-dihydroxypropyl)benzoic acid, solvate with water [5:1] (Isomer A).

A solution of ethyl-4-acetylaminobenzoate (Coneglio, L. *Rend. Acad. Sci. Napoli* [3] 1931, 36, 56–60) (2.07 g, 0.01 mol) and palladium acetate (1.12 g, 0.005 mol) in dry toluene (17 mL) was heated at reflux for 0.75 h under nitrogen. The solution was cooled to 60° C., the toluene was decanted, and the residue was washed with fresh toluene. The combined filtrates were heated at reflux for 3 h, the precipitate was collected by filtration, and mixed with the previous residue. The combined greenish residues were dried under vacuum for 3 h. To this residue, glacial acetic acid (40 mL) and allyl iodide (8.40 g, 0.05 mol) were added and the mixture was stirred at room temperature for 16 h. The palladium was removed by filtration through Celite and the filtrate was concentrated. The residue was passed through a column of silica gel using 1:1 ethyl acetate:hexane as eluent to give 0.85 g (69%) of ethyl-4-acetylamino-3-allylbenzoate as a white powder, mp 127°–128° C.

Analysis: Calculated for $C_{14}H_{17}NO_3$: C, 68.01; H, 6.88; N, 5.67 Found: C, 67.88; H, 6.93; N, 5.66

To a solution of 1:1 water and tert-butanol (10 mL), AD-mix-α (Aldrich, 1.4 g) was added and the mixture stirred for 0.1 h. The mixture had two layers; the lower layer was yellow in color. To this mixture, ethyl-4-acetylamino-3-allylbenzoate (0.1 g, 0.0004 mol) was added in one portion and stirred at room temperature for 48 h. The reaction mixture was cooled to 0° C. and sodium sulphite (1.5 g, 0.0119 mol) was added. The reaction was stirred at 0° C. for 0.3 h and then at room temperature for 0.5 h. It was extracted with ethyl acetate (3×15 mL), the combined organic layers were dried over sodium sulphate, filtered, and concentrated. The residue was passed through a column of silica gel eluting first with 1:1 ethyl acetate:hexane to recover the starting material, and then with pure ethyl acetate to give 0.075 g (66%) of ethyl-4-acetylamino-3-(2',3'-dihydroxypropyl)benzoate (isomer A) as a white powder, mp 114°–116° C. The optical rotation of this solid was 0° at 589 nm.

Analysis: Calculated for $C_{14}H_{19}NO_5$: C, 59.78; H, 6.76; N, 4.98 Found: C, 59.70; H, 6.79; N, 4.94

A solution of ethyl-4-acetylamino-3-(2',3'-dihydroxypropyl)benzoate (0.120 g, 0.00043 mol) in 1N sodium hydroxide (2 mL) was stirred at room temperature for 15 h. The solution was acidified with hydrochloric acid and concentrated under vacuum. The residue was dissolved in methanol (5 mL) and filtered. The filtrate was concentrated and the residue was passed through a column of silica gel using 85:15:1 mixture of ethyl acetate, methanol, and acetic acid to give 0.060 g (54%) of the title compound as an off-white powder, mp 181°–183° C.

Analysis: Calculated for $C_{12}H_{15}NO_5 \cdot 0.2 H_2O$: C, 56.10; H, 6.05; N, 5.46 Found: C, 56.09; H, 5.94; N, 5.41

EXAMPLE 36

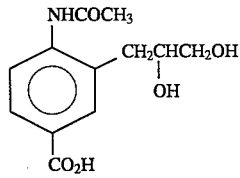

4-Acetylamino-3-(2',3'-dihydroxypropyl)benzoic acid, solvate with water [4:3](Isomer B).

A solution of ethyl-4-acetylaminobenzoate (Coneglio, L. *Rend Acad. Sci. Napoli* [3] 1931, 36, 56–60) (2.07 g, 0.01 mol) and palladium acetate (1.12 g, 0.005 mol) in dry toluene (17 mL) was heated at reflux for 0.75 h under nitrogen. The solution was cooled to 60° C., the toluene was decanted, and the residue was washed with fresh toluene. The combined filtrates were heated at reflux for 3 h, the precipitate was collected by filtration, and mixed with the previous residue. The combined greenish residues were dried under vacuum for 3 h. To this residue, glacial acetic acid (40 mL) and allyl iodide (8.40 g, 0.05 mol) were added and the mixture was stirred at room temperature for 16 h. The palladium was removed by filtration through Celite and the filtrate was concentrated. The residue was passed through a column of silica gel using 1:1 ethyl acetate:hexane as eluent to give 0.85 g (69%) of ethyl-4-acetylamino-3-allylbenzoate as a white powder, mp 127°–128° C.

Analysis: Calculated for $C_{14}H_{17}NO_3$: C, 68.01; H, 6.88; N, 5.67 Found: C, 67.88; H, 6.93; N, 5.66

To a solution of 1:1 water and tert-butanol (10 mL), AD-mix-β (Aldrich, 1.4 g) was added and the mixture stirred for 0.1 h. The mixture had two layers; the lower layer was yellow in color. To this mixture, ethyl-4-acetylamino-3-allylbenzoate (9.092 g, 0.00037 mol) was added in one portion and stirred at room temperature for 48 h. The reaction mixture was cooled to 0° C. and sodium sulphite (1.5 g, 0.0119 mol) was added. The reaction was stirred at 0° C. for 0.3 h and then at room temperature for 0.5 h. It was extracted with ethyl acetate (3×15 mL), the combined organic layers were dried over sodium sulphate, filtered, and concentrated. The residue was passed through a column of silica gel eluting first with 1:1 ethyl acetate:hexane to recover the starting material, and then with pure ethyl acetate to give 0.068 g (65%) of ethyl-4-acetylamino-3-(2',3'-dihydroxypropyl)benzoate (isomer B) as a white powder, mp 116°–117° C. The optical rotation of this solid was 0° C. at 589 nm.

Analysis: Calculated for $C_{14}H_{19}NO_5$: C, 59.78; H, 6.76; N, 4.98 Found: C, 59.73; H, 6.80; N, 5.01

A solution of ethyl-4-acetylamino-3-(2',3'-dihydroxypropyl)benzoate (0.090 g, 0.00032 mol) in 1N sodium hydroxide (2 mL) was stirred at room temperature for 15 h. The solution was acidified with hydrochloric acid and concentrated under vacuum. The residue was dissolved in methanol (5 mL) and filtered. The filtrate was concentrated and the residue was passed through a column of silica gel using a 85:15:1 mixture of ethyl acetate, methanol, and acetic acid to give 0.055 g (67%) of the title compound as an off-white powder, mp 180°–182° C.

Analysis: Calculated for $C_{12}H_{15}NO_5 \cdot 0.75 H_2O$: C, 54.03; H, 6.9; N, 5.25 Found: C, 54.19; H, 5.94; N, 5.32

EXAMPLE 37

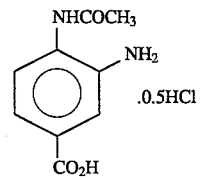

4-Acetylamino-3-aminobenzoic acid hydrochloride (2:1).

A mixture of ethyl 4-acetylamino-3-aminobenzoate (Blackburn, W., et al. *J. Org. Chem.* 1961, 26, 2805–2809) (1.0 g, 0.0045 mol) in 1N sodium hydroxide (10 mL, 0.01 mol) was stirred at 50° C. for 2 h. The mixture was filtered and acidified with concentrated hydrochloric acid. On standing overnight, a brown precipitate formed. The precipitate was separated by filtration and dried to give 0.7 g (73%) of the title compound as a brown powder, mp 272° C. (dec).

Analysis: Calculated for $C_9H_{10}N_2O_3 \cdot 0.5$ HCl: C, 50.89; H, 4.98; N, 13.18 Found: C, 50.54; H, 4.82; N, 13.01

EXAMPLE 38

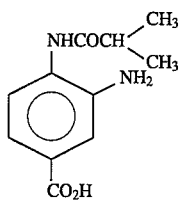

3-Amino-4-(2-methylpropionylamino)benzoic acid.

Ethyl 4-(2-methylpropionylamino)benzoate (Chemical Abstract 114(11) 101280u; Vagaonescu; Marisa, N-Acyl Derivatives of Anesthesin. *Stud Univ. Banes-Bolyai Chem.* 1989, 34, 12–14) was added slowly over a 50-min period to fuming nitric acid at 10° C. The reaction was stirred for 30 min at room temperature. Thin-layer chromatographic analysis (SiO$_2$, 1:1 ethyl acetate:hexane) showed disappearance of the starting material along with the formation of a new higher-running spot ($R_f$=0.9). The reaction was poured into water and then extracted with ethyl acetate (3×500 mL). Next, the organic layer was washed with 1% sodium bicarbonate (500 mL) solution and then water (500 mL). The ethyl acetate layer was concentrated and the residue chromatographed (SiO$_2$, 1:5 ethyl acetate:hexane). The fractions containing product were concentrated to give 17 g (49%) of ethyl 4-(2-methylpropionylamino)-3-nitrobenzoate as a yellow solid, mp 74°–76° C. An analytical sample was prepared by recrystallization from hexane. This material was collected by filtration and dried in vacuo at acetone reflux.

Analysis: Calculated for $C_{13}H_{16}N_2O_5$: C, 55.71; H, 5.71; N, 10.00 Found: C, 55.45; H, 5.85; N, 10.20

A sample of ethyl 4-(2-methylpropionylamino)-3-nitrobenzoate (8.0 g, 0.0286 mol) was suspended in ethanol (75 mL) containing platinum oxide (50 mg). The reaction mixture was hydrogenated for 2 h at 35 psi. Thin-layer chromatographic analysis (SiO$_2$, 1:1 hexane:ethyl acetate) showed disappearance of starting material along with the formation of a new lower-running spot ($R_f$=0.2). The mixture was then filtered through a pad of Celite and the pad washed with fresh ethanol. The filtrate was concentrated and the residue recrystallized from ethyl acetate-hexane. The solid was collected by filtration to give 5.0 g (70%) of ethyl 3-amino-4-(2-methylpropionylamino)benzoate. An analytical sample was prepared by recrystallization twice from ethyl acetate-hexane. The residue was collected by filtration and then dried in vacuo at acetone reflux to give a beige solid, mp 147°–149° C.

Analysis: Calculated for $C_{13}H_{18}N_2O_3$: C, 62.40; H, 7.20; N, 11.20 Found: C, 62.51; H, 7.28; N, 11.15

A sample of ethyl 3-amino-4-(2-methylpropionylamino)benzoate (2.30 g, 0.0092 mol) was suspended in 1N NaOH (13.80 mL, 0.0138 mol). After stirring for 24 h at room temperature the reaction was then heated at 50° C. for 6 h. The reaction was filtered and the filtrate acidified with 1N HCl forming an orange precipitate. The solid was collected by filtration and thin-layer chromatographic analysis (SiO$_2$, 9:1 ethyl acetate:methanol) indicated formation of a new lower-running spot ($R_f$=0.1). This material was recrystallized from N-butanol. The residue was collected by filtration and then suspended in ether. The product was filtered and dried in vacuo at acetone reflux to give 0.12 g (5%) of the title compound as a beige solid, mp 159°–160° C.

Analysis: Calculated for $C_{11}H_{14}N_2O_3$: C, 59.46; H, 6.31; N, 12.61 Found: C, 59.24; H, 6.43; N, 12.55

EXAMPLE 39

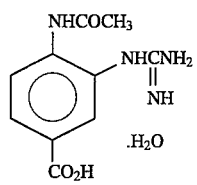

4-Acetylamino-3-[(aminoiminomethyl)amino]benzoic acid solvate with water (1:1).

A mixture of ethyl 4-acetylamino-3-aminobenzoate (Blackburn, W. et al. *J. Org. Chem.* 1961, 26, 2805–2809) (5.5 g, 0.025 mol), concentrated hydrochloric acid (2.1 mL, 0.025 moO, and cyanamide (21.0 g, 0.5 mol) in ethyl acetate (500 mL) was stirred at room temperature for 48 h and then heated at reflux for 2 h. On cooling, the white precipitate obtained was separated by filtration, washed with ethyl acetate, and dried to give 5.5 g (73%) of crude ethyl 4-acetylamino-3-[(aminoiminomethyl)amino]benzoate hydrochloride as a white powder. A mixture of ethyl 4-acetylamino-3-[(aminoiminomethyl)amino]benzoate hydrochloride (4.5 g, 0.015 mol) in sodium hydroxide (2.1 g in mL water) was stirred at room temperature for 48 h. The mixture was filtered through Celite to remove suspended particles. Concentrated hydrochloric acid was added to the filtrate to bring the pH close to 9. The precipitate was collected by filtration, washed with water, and dried to give 1.6 g (42%) of the title compound as a white powder, mp 260° C.

Analysis: Calculated for $C_{10}H_{12}N_4O_3 \cdot H_2O$: C, 47.24; H, 5.55; N, 22.04 Found: C, 47.00; H, 5.63; N, 21.94

EXAMPLE 40

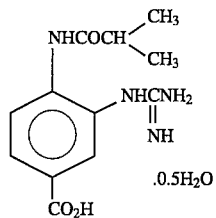

3-[(Aminoiminomethyl)amino]-4-(2-methylpropionylamino)benzoic acid hydrate [2:1].

Ethyl 4-(2-methylpropionylamino)benzoate was added slowly over a fifty-minute period to fuming nitric acid at 10° C. The reaction was stirred for 30 min at room temperature. Thin-layer chromatographic analysis (SiO$_2$, 1:1 ethyl acetate:hexane) showed disappearance of the starting material along with the formation of a new higher-running spot ($R_f$=0.9). The reaction was poured into water and then extracted with ethyl acetate (3×500 mL). Next, the organic layer was washed with 1% sodium bicarbonate (500 mL) solution and then water (500 mL). The ethyl acetate layer was concentrated and the residue chromatographed (SiO2, 1:5 ethyl acetate:hexane). The fractions containing product were concentrated to give 17 g (49%) of ethyl 4-(2-methylpropionylamino)-3-nitrobenzoate as a yellow solid, mp 74°–76° C. An analytical sample was prepared by recrystallization from hexane. This material was collected by filtration and dried in vacuo at acetone reflux.

Analysis: Calculated for $C_{13}H_{16}N_2O_5$: C, 55.71; H, 5.71; N, 10.00 Found: C, 55.45; H, 5.85; N, 10.20
(Chem. Abstract: 114(11) 101280u; Vagaonescu; Marisa. N-Acyl Derivatives of Anesthesin. *Stud. Univ. Banes-Bolyai, Chem.* 1989, 34, 12–14)

A sample of ethyl 4-(2-methylpropionylamino)-3-nitrobenzoate (8.0 g, 0.0286 mol) was suspended in ethanol (75 mL) containing platinum oxide (50 mg). The reaction mixture was hydrogenated for 2 h at 35 psi. Thin-layer chromatographic analysis ($SiO_2$, 1:1 hexane:ethyl acetate) showed disappearance of starting material along with the formation of a new lower-running spot ($R_f$=0.2). The mixture was then filtered through a pad of Celite and the pad washed with fresh ethanol. The filtrate was concentrated and the residue recrystallized from ethyl acetate-hexane. The solid was collected by filtration to give 5.0 g (70%) of ethyl 3-amino-4-(2-methylpropionylamino)benzoate. An analytical sample was prepared by recrystallization twice from ethyl acetate-hexane. The residue was collected by filtration and then dried in vacuo at acetone reflux to give a beige solid, mp 147°–149° C.

Analysis: Calculated for $C_{13}H_{18}N_2O_3$: C, 62.40; H, 7.20; N, 11.20 Found: C, 62.51;H, 7.28;N, 11.15

To ethyl 3-amino-4-(2-methylpropionylamino)benzoate (1.7 g, 0.0068 mol) dissolved in ethyl acetate (50 mL) was added concentrated HCl (0.57 mL, 0.0068 mol) and cyanamide (5.71 g, 0.136 mol). The solution was heated at reflux for 48 h. Thin-layer chromatographic analysis ($SiO_2$, 9:1 ethyl acetate:methanol) showed starting material (35%) along with the formation of a new lower-running spot ($R_f$=0.1). The material was concentrated and dried in vacuo overnight. The resulting solid was passed through a 350-mL frit funnel ($SiO_2$) using ethyl acetate to elute the higher-running spots. Next, the solvent concentration was stepped up to 17:3 ethyl acetate:methanol in order to elute the product. The filtrates were concentrated and the residue suspended in ethyl acetate. The resulting solid was collected by filtration to give 0.76 g (34%) of ethyl 3-[(aminoiminomethyl)amino]-4-(2-methylpropionylamino)benzoate hydrochloride as a pale yellow solid. An analytical sample was prepared by recrystallizing a portion of the residue from methanol-ether. This sample was collected by filtration and dried over toluene in vacuo to give a white solid, mp 175°–177° C.

Analysis: Calculated for $C_{14}H_{20}N_4O_3 \cdot HCl \cdot 0.5\ H_2O$: C, 49.79; H, 6.52; N, 16.60 Found: C, 49.97; H, 6.57; N, 16.68

A sample of ethyl 3-[(aminoiminomethyl)amino]-4-(2-methylpropionylamino)benzoate hydrochloride (0.36 g, 0.0012 mol) was suspended in 1N NaOH (1.85 mL, 0.0019 mol). After stirring for 1 h at 38° C., additional 1N NaOH (0.5 mL, 0.0005 mol) was added and the reaction was allowed to stir for 1 h more. Thin-layer chromatographic analysis ($SiO_2$, 4:1 ethyl acetate-methanol) indicated that starting material had reacted to form a new lower-running spot ($R_f$=0.1). The pH was adjusted to 7.0 with 1N HCl causing formation of a white precipitate. The solid was collected by filtration. It was purified by dissolving again in a minimum amount of 1N NaOH and adjusting the pH to 7.0 with dilute HCl causing formation of a white precipitate. The solid was collected by filtration and dried in vacuo at toluene reflux to give 0.15 g (52%) of the title compound as a white solid, mp 238°–239.5° C.

Analysis: Calculated for $C_{12}H_{16}N_4O_3 \cdot 0.5\ H_2O$: C, 52.75; H, 6.23;N, 20.51 Found: C, 52.70; H, 6.30; N, 20.44

EXAMPLE 41

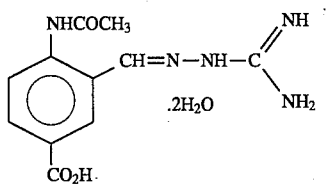

4-Acetylamino-3-{[(aminoiminomethyl)hydrazino]methylene}benzoic acid dihydrate.

A mixture of methyl 4-acetylamino-3-formylbenzoate (Gassman, P. G.; Drews, H. R. *J. Amer. Chem. Soc.* 1978, 100, 7600–7610) (2.21 g, 0.01 mol), aminoguanidine bicarbonate (1.40 g, 0.0102 mol) and concentrated hydrochloric acid (1.68 mL, 0.02 mol) in ethanol (50 mL) was heated to reflux for 4 h. The reaction mixture was cooled and the white precipitate was collected by filtration. The filtrate on concentration and cooling gave more precipitate which was again collected by filtration. Both precipitates were combined and dried to give 2.1 g (69%) of methyl 4-acetylamino-3-{[(aminoiminomethyl)hydrazino]methylene}benzoate hydrochloride as a fluffy white powder, mp 278° C.

Analysis: Calculated for $C_{12}H_{15}N_5O_3 \cdot HCl$: C, 45.94; H, 5.14; N, 22.32 Found: C, 46.24; H, 5.18; N, 22.46

A mixture of methyl 4-acetylamino-3-{[(aminoiminomethyl)hydrazino]methylene}benzoate hydrochloride (0.54 g, 0.0017 mol) and 1N sodium hydroxide (5.0 mL, 0.005 mol) was stirred at room temperature for 24 h. After filtration, the mixture was neutralized with concentrated hydrochloric acid. The precipitate was collected by filtration, washed with water, and dried over toluene under vacuum to give 0.41 g (80%) of the title compound as a white powder, mp 326°–327° C.

Analysis: Calculated for $C_{11}H_{13}N_5O_3 \cdot 2\ H_2O$: C, 44.15; H, 5.73; N, 23.40 Found: C, 44.20; H, 5.48; N, 23.16

EXAMPLE 42

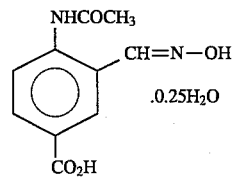

4-Acetylamino-3-[(hydroxylimino)methyl]benzoic acid hydrate (4:1).

A mixture of methyl 4-acetylamino-3-formylbenzoate (Gassman, P. G.; Drews, H. R. *J. Am. Chem. Soc.* 1978, 100, 7600–7610) (0.442 g, 0.002 mol) and hydroxylamine hydrochloride (0.174 g, 0.0025 mol) in ethyl acetate (10 mL) was heated at reflux for 16 h. White precipitate formed which was removed by filtration and the filtrate was concentrated to dryness. The residue was recrystallized from ethyl acetate-hexane to give 0.25 g (53%) of methyl 4-acetylamino-3-[(N-hydroxylimino)methyl]benzoate as a pale yellow powder, mp 200°–203° C.

Analysis: Calculated for $C_{11}H_{12}N_2O_4$: C, 55.93; H, 5.12;N, 11.86 Found: C, 56.08; H, 5.19; N, 11.72

A mixture of methyl 4-acetylamino-3-[(hydroxylimino)methyl]benzoate (142 mg, 0.6 mmol) and 1N sodium hydroxide (1.0 mL, 1.0 mmol) was stirred at room temperature for 4 h. The mixture was filtered through a pad of cotton and neutralized with dil. hydrochloric acid. The precipitate obtained was collected by filtration, washed with water, and dried under vacuum over acetone for 24 h to give 95 mg (71%) of the title compound as a white powder, mp 215°–218° C. (dec).

Analysis: Calculated for $C_{10}H_{10}N_2O_4 \cdot 0.25\ H_2O$: C, 52.98; H, 4.67; N, 12.36 Found: C, 52.92; H, 4.66; N, 12.26

EXAMPLE 43

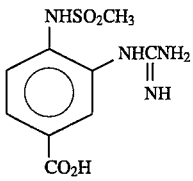

3-[(Aminoiminomethyl)amino]-4-[(methylsulfonyl)amino] benzoic acid, solvate with water (2:1).

Ethyl 4-[(methylsulfonyl)amino]benzoate (Lumma, W. C. et al. *J. Med. Chem.* 1987, 30, 758–763) (2.0 g, 0.0082 mol) was added portionwise to fuming nitric acid (10 mL) at 5°–10° C. over 0.25 h. The mixture was further stirred for 0.5 h at 10°–15° C. and then poured into cold water (50 mL). The yellow precipitate was separated by filtration and washed several times with cold water. The cake was recrystallized from ethyl acetate to give 1.7 g (72%) of ethyl 3-nitro-4-[(methylsulfonyl)amino]benzoate as yellow crystals, mp 124° C.

Analysis: Calculated for $C_{10}H_{12}N_2O_6S$: C, 41.66; H, 4.20; N, 9.72 Found: C, 41.30; H, 4.15; N, 9.86

Ethyl 3-nitro-4-[(methylsulfonyl)amino]benzoate (1.0 g, 0.0035 mol) was dissolved in ethanol (40 mL) and hydrogenated at 20 psi in the presence of platinum oxide (Aldrich, 0.02 g) for 1 h. The catalyst was removed by filtration through Celite and the filtrate was concentrated to 20 mL. On cooling, a precipitate formed which was separated by filtration, washed with cold ethanol, and dried to give 0.75 g (84%) of ethyl 3-amino-4-[(methylsulfonyl)amino]benzoate as a white powder, mp 151° C.

Analysis: Calculated for $C_{10}H_{14}N_2O_4S$: C, 46.50; H, 5.46; N, 10.84 Found: C, 46.52; H, 5.50; N, 10.92

A mixture of ethyl 3-amino-4-[(methylsulfonyl)amino] benzoate (2.58 g, 0.01 mol), concentrated hydrochloric acid (0.84 mL, 0.01 mol), and cyanamide (4.2 g, 0.1 mol) in ethyl acetate (100 mL) was heated at reflux for 4 h. The reaction mixture was cooled and the white precipitate separated by filtration. The cake was washed several times with cold ethyl acetate and dried under vacuum to give 2.95 g (85.5%) of ethyl 3-[(aminoiminomethyl)amino]-4-[(methylsulfonyl)amino]benzoate hydrochloride as a white powder, mp 160°–164° C.

Analysis: Calculated for $C_{11}H_{16}N_4S \cdot HCl \cdot 0.5\ H_2O$: C, 38.21; H, 5.25; N, 16.20 Found: C, 38.42; H, 5.32; N, 16.00

A mixture of ethyl 3-[(aminoiminomethyl)amino]-4-[(methylsulfonyl)amino]benzoate (1.80 g, 0.0052 mol) in 1.5N sodium hydroxide (15 mL, 0.0225 mol) was stirred at room temperature for 4 h. The mixture was neutralized with concentrated hydrochloric acid to give an off-white precipitate. The precipitate was separated by filtration, washed with water, and dried to give 1.19 g (81%) of the title compound as an off-white powder, mp 200° C.

Analysis: Calculated for $C_9H_{12}N_4O_4S \cdot 0.5\ H_2O$: C, 38.43; H, 4.66; N, 19.92 Found: C, 38.60; H, 4.64; N, 19.90

EXAMPLE 44

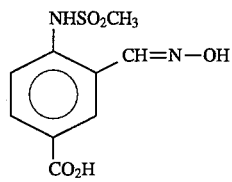

3-[(N-Hydroxyimino)methyl]-4-[(methylsulfonyl)amino] benzoic acid.

To 2-amino-5-(methoxycarbonyl)benzaldehyde trimethylene mercaptal (Gassman, P. G.; Drews, H. R. *J. Am. Chem. Soc.* 1978, 100, 7600–7610) (5.0 g, 0.019 mol) in dichloromethane (90 mL) was added pyridine (4.51 mL, 0.055 mol). Methanesulfonyl chloride (4.31 mL, 0.055 mol) was then added over a five-minute period and the reaction mixture heated at reflux overnight. Thin-layer chromatography analysis (SiO$_2$, EtOAc:hexane 1:1) showed the disappearance of the starting material along with the appearance of a new lower-running spot ($R_f$=0.56) indicating the reaction was complete. Upon cooling, the reaction was washed thoroughly with 10% acetic acid followed by water. The organic layer was dried (Na$_2$SO$_4$), filtered, and concentrated. The crude residue was placed on a SiO$_2$ column and eluted with 1:1 EtOAc:hexane. Fractions containing the desired product were combined and concentrated to yield 5.0 g (77%) of 2-(methanesulfonylamino)-5-(methoxycarbonyl)benzaldehyde trimethylene mercaptal as a yellow solid. An analytical sample, mp 168°–168.5° C., was recrystallized from ethanol.

Analysis: Calculated for $C_{13}H_{17}NO_4S_3$: C, 44.94; H, 4.93; N, 4.03 Found: C, 44.98; H, 4.94; N, 4.01

A sample of 2-(methanesulfonylamino)-5-(methoxycarbonyl)benzaldehyde trimethylene mercaptal (7.66 g, 0.022 mol) dissolved in N,N-dimethylformamide (4.35 mL) and acetone (39.13 mL) was added over a 5-min period through a dropping funnel to a solution of copper (II) oxide (2.09 g, 0.026 mol), copper (II) chloride (7.0 g, 0.055 mol) in acetone (174.0 mL) and heated at reflux. After 2 h at reflux, thin-layer chromatography analysis (SiO$_2$, EtOAc:hexane 1:1) showed disappearance of the starting material and the appearance of a new slightly higher $R_f$ spot which gave a positive result when sprayed with 2,4-DNP. Upon cooling, the reaction was filtered through Celite and the cake was washed with 10% ethanol in dichloromethane. Water (125 mL) and dichloromethane (150 mL) were added to the filtrate. The layers were partitioned and the water layer extracted 2×100 mL dichloromethane. The combined organic layers were washed twice with water (100 mL), dried (Na$_2$SO$_4$), and filtered. Concentration of the filtrate gave a beige solid which was dried in vacuo to give 4.48 g (79%) of 2-(methanesulfonylamino)-5-(methoxycarbonyl)benzaldehyde, mp 161°–163° C. (ethanol).

Analysis: Calculated for $C_{10}H_{11}NO_5S$: C, 46.69; H, 4.28; N, 5.44 Found: C, 46.67; H, 4.35; N, 5.46

A mixture of 2-(methanesulfonylamino)-5-(methoxycarbonyl)benzaldehyde (2.56 g, 0.01 mol) and hydroxylamine hydrochloride (0.87 g, 0.0125 mol) in ethanol (40 mL) was heated at reflux for 2 h. The mixture was filtered hot, and the filtrate was concentrated to dryness. The residue was suspended in water. The solid was collected by filtration and recrystallized from ethyl acetate-hexane to give 2.42 g (89%) of methyl 3-[(N-hydroxyimino)methyl]-4-[(methylsulfonyl)amino]benzoate as an off-white powder, mp 160° C.

Analysis: Calculated for $C_{10}H_{12}N_2O_5S$: C, 44.11; H, 4.44; N, 10.29 Found: C, 44.07; H, 4.45; N, 10.20

EXAMPLE 45

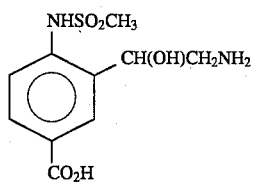

3-[2-Amino-1-(R,S)-hydroxyethyl]-4-[(methylsulfonyl)amino]benzoic acid hydrate (5:1).

To 2-amino-5-(methoxycarbonyl)benzaldehyde trimethylene mercaptal (Gassman, P. G.; Drews, H. R. *J. Am. Chem. Soc.* 1978, 100, 7600–7610) (5.0 g, 0.019 mol) in dichloromethane (90 mL) was added pyridine (4.51 mL, 0.055 mol). Methanesulfonyl chloride (4.31 mL, 0.055 mol) was then added over a 5-min period and the reaction mixture heated at reflux overnight. Thin-layer chromatography analysis (SiO$_2$, EtOAc:hexane 1:1) showed the disappearance of the starting material along with the appearance of a new lower-running spot (R$_f$=0.56) indicating the reaction was complete. Upon cooling, the reaction was washed thoroughly with 10% acetic acid followed by water. The organic layer was dried (Na$_2$SO$_4$), filtered, and concentrated. The crude residue was placed on a SiO$_2$ column and eluted with 1:1 EtOAc:hexane. Fractions containing the desired product were combined and concentrated to yield 5.0 g (77%) of 2-(methanesulfonylamino)-5-(methoxycarbonyl)benzaldehyde trimethylene mercaptal as a yellow solid. An analytical sample, mp 168°–168.5° C. was recrystallized from ethanol.

Analysis: Calculated for C$_{13}$H$_{17}$NO$_4$S$_3$: C, 44.94; H, 4.93; N, 4.03 Found: C, 44.98; H, 4.94; N, 4.01

A sample of 2-(methanesulfonylamino)-5-(methoxycarbonyl)benzaldehyde trimethylene mercaptal (7.66 g, 0.022 mol) dissolved in N,N-dimethylformamide (4.35 mL) and acetone (39.13 mL) was added over a 5-min period through a dropping funnel to a solution of copper (II) oxide (2.09 g, 0.026 mol), copper (II) chloride (7.0 g, 0.055 mol) in acetone (174.0 mL), and heated at reflux. After 2 h at reflux, thin-layer chromatography analysis (SiO$_2$, EtOAc:hexane 1:1) showed disappearance of the starting material and the appearance of a new slightly higher R$_f$ spot which gave a positive result when sprayed with 2,4-DNP. Upon cooling, the reaction was filtered through Celite and the cake was washed with 10% ethanol in dichloromethane. Water (125 mL) and dichloromethane (150 mL) were added to the filtrate. The layers were partitioned and the water layer extracted 2×100 mL dichloromethane. The combined organic layers were washed twice with water (100 mL), dried (Na$_2$SO$_4$), and filtered. Concentration of the filtrate gave a beige solid which was dried in vacuo to give 4.48 g (79%) of 2-(methanesulfonylamino)-5-(methoxycarbonyl)benzaldehyde, mp 161°–163° C. (ethanol).

Analysis: Calculated for C$_{10}$H$_{11}$NO$_5$S: C, 46.69; H, 4.28; N, 5.44 Found: C, 46.67; H, 4.35; N, 5.46

Nitromethane (1.22 g, 0.02 mol) was added to an ice-cooled mixture of 2-(methanesulfonylamino)-5-(methoxycarbonyl)benzaldehyde (2.57 g, 0.01 mol) in ethanol and the mixture stirred for 10 min. To this mixture was added potassium hydroxide (1.23 g, 0.022 mol in 20 mL 90% ethanol) at 0° C. over a period of 20 min. The reaction mixture was further stirred at 0° C. for 0.5 h and then at room temperature for 4 h. The mixture was neutralized with 2N HCl and poured in water (100 mL). The mixture was extracted with chloroform, dried over sodium sulfate, filtered, and concentrated. The residue was passed through a column of silica gel eluting with chloroform:methanol (99:1 to 95:5). The desired pure fractions were combined, concentrated, recrystallized from ethyl acetate-hexane, and dried to give 0.8 g (25%) of methyl 3-[1-(R,S)-hydroxy-2-nitroethyl]-4-[(methylsulfonyl)amino]benzoate as off-white crystals, mp 148° C.

Analysis: Calculated for C$_{11}$H$_{14}$N$_2$O$_7$S: C, 41.51; H, 4.43; N, 8.80 Found: C, 41.68; H, 4.50; N, 8.78

Methyl 3-[1-(R,S)-hydroxy-2-nitroethyl]-4-[(methylsulfonyl)amino]benzoate (200 mg, 0.63 mmol) was dissolved in ethanol (10 mL) and hydrogenated at 50 psi in the presence of platinum oxide (Aldrich, 20 mg) for 8 h. The catalyst was removed by filtration through Celite and the filtrate concentrated to 5 mL. To the concentrate, ethyl acetate (5 mL) and hexane (10 mL) were added and the mixture cooled to 0° C. A white precipitate formed which was collected by filtration. The cake was washed with ethyl acetate:hexane (1:1) and dried to give 100 mg (55%) of methyl 3-[2-amino-1-(R,S)-hydroxyethyl]-4-[(methylsulfonyl)amino]benzoate as a white powder, mp 172°–173° C. (dec).

Analysis: Calculated for C$_{11}$H$_{16}$N$_2$O$_5$S: C, 45.82; H, 5.59; N, 9.72 Found: C, 45.84; H, 5.72; N, 9.30

A mixture of methyl 3-[2-amino-1-(R,S)-hydroxyethyl]-4-[(methylsulfonyl)amino]benzoate (50 mg, 0.17 mmol) in 1N sodium hydroxide (44 µL, 0.44 mmol) was stirred at room temperature for 4 h. The mixture was neutralized with dilute hydrochloric acid and let stand overnight at room temperature. A white precipitate accumulated which was collected by filtration, washed with water, and dried to give 38 mg (81%) of the title compound as a white powder, mp 274°–276° C.

Analysis: Calculated for C$_{10}$H$_{14}$N$_2$O$_5$S.0.2 H$_2$O: C, 43.22; H, 5.22; N, 10.08 Found: C, 43.13; H, 5.26; N, 9.95

EXAMPLE 46

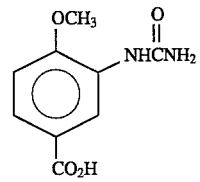

3-[(Aminoiminomethyl)amino]-4-methoxybenzoic acid hydrochloride (1:1).

A mixture of 3-amino-4-methoxybenzoic acid (Aldrich, 1.67 g, 0.01 mol), hydrochloric acid (12N, 0.84 mL, 0.01 mol), and cyanamide (0.84 g, 0.02 mol) in absolute ethanol (20 mL) was heated at reflux for 2 h. The mixture was cooled and the precipitate separated by filtration. The cake was washed several times with ether and dried under vacuum to give 1.60 g (65%) of the title compound as a white powder, mp 322° C. (dec).

Analysis: Calculated for C$_9$H$_{11}$N$_3$O$_3$.HCl: C, 44.00; H, 4.95; N, 17.10 Found: C, 44.30; H, 4.94; N, 16.86

EXAMPLE 47

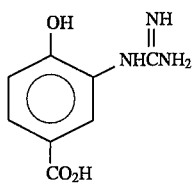

3-[(Aminoiminomethyl)amino]-4-hydroxybenzoic acid hydrochloride (1:1).

A mixture of 3-amino-4-hydroxybenzoic acid (Aldrich, 1.53 g, 0.01 mol), hydrochloric acid (12N, 0.84 mL, 0.01 mol), and cyanamide (0.84 g, 0.02 mol) in absolute ethanol (20 mL) was stirred at room temperature for 48 h and then heated at reflux for 6 h. The mixture was allowed to stand in the refrigerator for 4 weeks during which time a brown solid began to form. The solid was collected by filtration and washed several times with ether. The solid was then dried under vacuum to give 0.32 g (14%) of the title compound as a brown powder, mp 254° C.

Analysis: Calculated for $C_8H_9N_3O_3.HCl$: C, 41.48; H, 4.35; N, 18.14 Found: C, 41.66; H, 4.58; N, 18.12

EXAMPLE 48

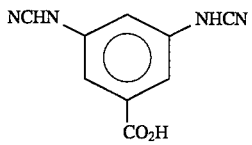

3,5-Dicyanaminobenzoic acid.

To a solution of 3,5-diaminobenzoic acid (Aldrich, 3.8 g, 25 mmol) in acetic acid:water (1:1, 30 mL) was added sodium acetate (4.1 g, 50 mmol). The resulting mixture was cooled to 0° C. and cyanogen bromide (6.5 g, 60 mmol) was added in two portions over a period of 10 min. The reaction mixture was allowed to warm to room temperature and stirred overnight at this temperature. The reaction mixture was poured into 130 g ice. The precipitate was collected by filtration and washed with cold water and dried in vacuo to give 4.43 g crude product. The product was dissolved in methanol and concentrated to half its volume and cooled. The product obtained was collected by filtration to give 2.51 g (50%) of the title compound as a grayish-white solid, mp>300° C. (dec).

Analysis: Calculated for $C_9H_6N_4O_2$: C, 53.46; H, 3.00; N, 27.70 Found: C, 53.28; H, 3.17; N, 27.43

EXAMPLE 49

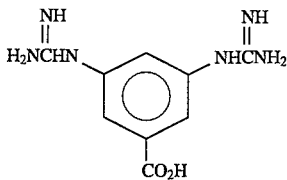

3,5-Bis-[(aminoiminomethyl)amino]benzoic acid hydrochloride, solvate with ethanol (10:15:2).

A mixture of 3,5-diaminobenzoic acid dihydrochloride semihydrate (Aldrich, 2.32 g, 0.01 mol) and cyanamide (2.52 g, 0.06 mol) in absolute ethanol (50 mL) was heated at reflux for 8 h. The mixture was cooled and the precipitate separated by filtration. The cake was washed several times with ethanol and dried under vacuum to give 2.20 g (73%) of the title compound as an off-white powder, mp 280° C. (dec).

Analysis: Calculated for $C_9H_{12}N_6O_2.1.5\ HCl.0.2\ EtOH$: C, 37.62; H, 4.94; N, 28.00 Found: C, 37.96; H, 5.06; N, 27.75

EXAMPLE 50

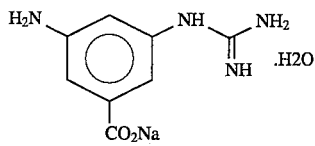

Sodium 3-amino-5-[(aminoimino)methyl]aminobenzoate hydrate.

To a solution of ethyl 3,5-diaminobenzoate (Pfaltz & Bauer, 1.8 g, 10 mmol) in DMF (8 mL) was added triethylamine (4.91 mL, 35 mmol) and bisboc thiourea (2.76 g, 10 mmol). The resulting mixture was cooled to 0° C. and mercuric chloride (2.99 g, 11 mmol) was added. The reaction mixture was stirred at 0° C. for 30 min and then at room temperature for 24 h. Ethyl acetate (75 mL) was added and the slurry filtered through Celite. The filtrate was washed with water (4×15 mL) and the organic layer dried ($Na_2SO_4$), filtered, and solvent removed in vacuo to give 4.95 g of crude product. The crude product was purified by flash column chromatography (10–20% ethyl acetate in hexane) to obtain 2.51 g (60%) of ethyl 3-amino-5-[(t-butoxycarbonylamino-t-butoxycarbonylimino)methyl]aminobenzoate as a white solid, mp 126°–128° C.

Analysis: Calculated for $C_{20}H_{30}N_4O_6$: C, 56.85; H, 7.17; N, 13.26 Found: C, 56.83; H, 7.21; N, 13.19

To a solution ethyl-3-amino-5-[(t-butoxycarbonylamino-t-butoxycarbonylimino)methyl]aminobenzoate (1.8 g, 4.25 mmol) in methylene chloride (20 mL) at 0° C. was added dropwise trifluoroacetic acid (3.27 mL, 42.5 mmol) and the solution stirred at room temperature for 6 h. After 6 h, additional trifluoroacetic acid (3.27 mL, 42.5 mmol) was added and the reaction stirred overnight at room temperature. The solvent was removed in vacuo and the excess trifluoroacetic acid was removed by co-distilling twice with methylene chloride (20 mL). The resulting oily residue was dissolved in 3M NaOH (67.5 mmol, 22.5 mL) and stirred at room temperature for 45 min. The pH was adjusted between 7–8 using 1N HCl solution. The clear solution was warmed and filtered and concentrated to half its volume. The product which was obtained on standing at room temperature for 2 h was collected by filtration, washed with a small amount of methanol and ether, and dried in a pistol at toluene reflux overnight in vacuo to furnish 0.66 g (66%) of the title compound as a white solid, mp 198°–203° C.

Analysis: Calculated for $C_8H_9N_4NaO_2.H_2O$: C, 41.02; H, 4.74; N, 23.93 Found: C, 41.23; H, 5.06; N, 23.75

EXAMPLE 51

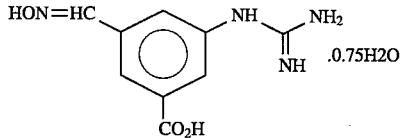

3-[(Aminoiminomethyl)amino]-5-[(N-hydroxylimino)methyl]benzoic acid hydrate (4:3).

Oxalyl chloride (5.0 mL, 0.057 mol) was added to a solution of dimethylformamide (1.46 g, 0.02 mol) in dichloromethane (30 mL) at 0° C. and the reaction mixture was stirred at this temperature for 1 h. The solvent was removed under a reduced pressure. The residual white powder was suspended in tetrahydrofuran (50 mL) and acetonitrile (30 mL) and to this mixture was added a solution of 3-carbomethoxy-5-nitrobenzoic acid (Holy, G. B. *J. Med. Chem.* 1963, 6, 24–26) (4.5 g, 0.02 mol) and pyridine (1.58 g, 0.02 mol) in tetrahydrofuran (10 mL) at −30° C. over a period of 10 min. The reaction mixture was stirred further for 1 h at −30° C. and a suspension of copper (I) iodide (0.381 g, 0.002 mol) in tetrahydrofuran (10 mL) was added to it. The reaction mixture was cooled to −78° C. and a solution of lithium tri-tert-butoxyaluminohydride (Aldrich, 1.0M in tetrahydrofuran, 40.0 mL, 0.04 mol) was added over a period of 10 min. It was further stirred for 10 min at −78° C. To this mixture was added aqueous hydrochloric acid (2N, 50 mL) and the organic layer separated, washed with sodium bicarbonate solution, dried over sodium sulphate, filtered, and concentrated to dryness. The residue was passed through a column of silica gel using ethyl acetate:hexane (1:2) as eluent. Fraction 1 [$R_f$=0.55 in ethyl acetate:hexane (1:2)] gave 0.25 g (6%) of methyl 3-formyl-5-nitrobenzoate as an off-white solid, mp 85° C.

Analysis: Calculated For $C_9H_7NO_5$: C, 51.68; H, 3.37; N, 6.70 Found: C, 51.63; H, 3.48; N, 6.57

A mixture of methyl 3-formyl-5-nitrobenzoate (0.418 g, 2.0 mmol), hydroxylamine hydrochloride (0.209 g, 3.0 mmol) in ethanol (5.0 mL) was heated at reflux for 2 h. On cooling, the mixture was poured into water and the precipitate collected by filtration. The cake was recrystallized from ethyl acetate-hexane and dried to give 0.22 g (49%) of methyl 3-[(N-hydroxylimino)methyl]-5-nitrobenzoate as an off-white solid, mp 144°–145° C.

Analysis: Calculated for $C_9H_9N_2O_5$: C, 48.22; H, 3.60; N, 12.50 Found: C, 48.22; H, 3.61; N, 12.41

A mixture of methyl 3-[(N-hydroxylimino)methyl]-5-nitrobenzoate (2.0 g, 0.009 mol) in ethanol (150 mL) was hydrogenated in the presence of platinum oxide (0.25 g) at 30 psi for 0.5 h. The catalyst was removed by filtration through Celite and the filtrate was concentrated. The residue was recrystallized from ethyl acetate-hexane to give 1.1 g (64%) of methyl 3-amino-5-[(N-hydroxylimino)methyl] benzoate as an off-white solid, mp 160°–162° C.

Analysis: Calculated for $C_9H_{10}N_2O_3$: C, 55.67; H, 5.19; N, 14.42 Found: C, 55.55; H, 5.33; N, 14.00

A mixture of methyl 3-amino-5-[(N-hydroxylimino)methyl]benzoate (0.97 g, 0.005 mol), N,N-bis(tert-butoxycarbonyl)thiourea (1.52 g, 0.0055 mol) and triethylamine (1.77 g, 0.0175 mol) in dimethylformamide (10.0 mL) was cooled to 5° C. Mercuric chloride (1.49 g, 0.0055 mol) was added to the mixture and stirred at 5° C. for 0.5 h and then at room temperature for 18 h. The mixture was diluted with ethyl acetate (40 mL) and filtered through Celite. The filtrate was washed with water and the organic layer dried over sodium sulphate. The mixture was filtered, the filtrate concentrated, and the residue was passed through a column of silica gel using ethyl acetate:hexane (1:3 to 1:1). The appropriate fractions were pooled, combined, and concentrated to give methyl 3-{[(tert-butoxycarbonylamino-tert-butoxycarbonylimino)methyl]amino}-5-[(N-hydroxylimino)methyl]benzoate [$R_f$=0.7 in ethyl acetate:hexane (1:1)]. An analytical sample was recrystallized from ethyl acetate:hexane to give 0.7 g (30%) as a white solid, mp 158°–160° C. (dec).

Analysis: Calculated for $C_{20}H_{28}N_4O_7$: C, 55.04; H, 6.47; N, 12.84 Found: C, 55.48; H, 6.65; N, 12.72

A mixture of methyl 3-{[(tert-butoxycarbonylamino-tert-butoxycarbonylimino)methyl]amino}-5-[(N-hydroxylimino)methyl]benzoate (360 mg, 0.83 mmol) and trifluoroacetic acid (1.5 mL) in dichloromethane (15 mL) was stirred at room temperature for 24 h. The mixture was concentrated and the residue was repeatedly evaporated with dichloromethane.

The residue was suspended in sodium hydroxide (1N, 3.0 mL, 3.0 mmol) and stirred for 6 h. The pH of the mixture was adjusted to close to 8 with dilute hydrochloric acid. White solid separated out, which was collected by filtration, washed with water, and dried under vacuum over toluene to give 125 mg (64%) of the title compound as an off-white solid, mp 248°–253° C. (dec).

Analysis: Calculated for $C_9H_{10}N_4O_3 \cdot 0.75\ H_2O$: C, 45.86; H, 4.92; N, 23.77 Found: C, 46.00; H, 4.92; N, 23.72

EXAMPLE 52

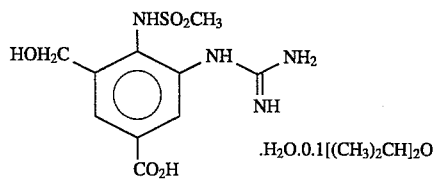

3-(Aminoiminomethyl)amino-5-hydroxymethyl-4-(methylsulfonyl)aminobenzoic acid hydrate complex with diisopropyl ether (10:10:1).

To 2-amino-5-(methoxycarbonyl)benzaldehyde trimethylene mercaptal (Gassman, P. G.; Drews, H. R. *J. Am. Chem. Soc.* 1978, 100, 7600–7610) (5.0 g, 0.019 mol) in dichloromethane (90 mL) was added pyridine (4.51 mL, 0.055 mol). Methanesulfonyl chloride (4.31 mL, 0.055 mol) was then added over a 5-min period and the reaction mixture heated at reflux overnight. Thin-layer chromatography analysis ($SiO_2$, EtOAc:hexane 1:1) showed the disappearance of the starting material along with the appearance of a new lower-running spot ($R_f$=0.56) indicating the reaction was complete. Upon cooling, the reaction was washed thoroughly with 10% acetic acid followed by water. The organic layer was dried ($Na_2SO_4$), filtered, and concentrated. The crude residue was placed on a $SiO_2$ column and eluted with 1:1 EtOAc:hexane. Fractions containing the desired product were combined and concentrated to yield 5.0 g (77%) of 2-(methanesulfonylamino)-5-(methoxycarbonyl)benzaldehyde trimethylene mercaptal as a yellow solid. An analytical sample, mp 168°–168.5° C., was recrystallized from ethanol.

Analysis: Calculated for $C_{13}H_{17}NO_4S_3$: C, 44.94; H, 4.93; N, 4.03 Found: C, 44.98; H, 4.94; N, 4.01

A sample of 2-(methanesulfonylamino)-5-(methoxycarbonyl)benzaldehyde trimethylene mercaptal (7.66 g, 0.022 mol) dissolved in N,N-dimethylformamide (4.35 mL) and acetone (39.13 mL) was added over a 5-min period through a dropping funnel to a solution of copper (II) oxide (2.09 g, 0.026 mol), copper (II) chloride (7.0 g, 0.055 mol) in acetone (174.0 mL), and heated at reflux. After 2 h at reflux, thin-layer chromatography analysis ($SiO_2$, EtOAc:hexane 1:1) showed disappearance of the starting material and the appearance of a new slightly-higher $R_f$ spot which gave a positive result when sprayed with 2,4-DNP. Upon cooling, the reaction was filtered through Celite and the cake was washed with 10% ethanol in dichloromethane. Water (125 mL) and dichloromethane (150 mL) were added to the filtrate. The layers were partitioned and the water layer extracted 2×100 mL dichloromethane. The combined organic layers were washed twice with water (100 mL), dried ($Na_2SO_4$), and filtered. Concentration of the filtrate gave a beige solid which was dried in vacuo to give 4.48 g (79%) of 2-(methanesulfonylamino)-5-(methoxycarbonyl-)benzaldehyde, mp 161°–163° C. (ethanol).

Analysis: Calculated for $C_{10}H_{11}NO_5S$: C, 46.69; H, 4.28; N, 5.44 Found: C, 46.67; H, 4.35; N, 5.46

Methyl 3-formyl-4-[(methylsulfonyl)amino]benzoate (3.85 g, 0.015 mol) was added portionwise to fuming nitric acid (45 mL) at 5°–10° C. over 0.25 h. The mixture was further stirred for 1.0 h at room temperature and then poured into cold water (200 mL). The yellow precipitate was collected by filtration and washed several times with cold water. The cake was recrystallized from ethyl acetate-hexane to give 2.5 g (55.3%) of methyl 3-formyl-4-[(methylsulfonyl)amino]-5-nitrobenzoate as light yellow needles, mp 158°–160° C.

Analysis: Calculated for $C_{10}H_{10}N_2O_7S$: C, 39.74; H, 3.33; N, 9.27 Found: C, 39.56; H, 3.30; N, 9.23

Methyl 3-formyl-4-[(methylsulfonyl)amino]-5-nitrobenzoate (2.0 g, 0.0066 mol) was dissolved in ethanol (50 mL) and hydrogenated at 30 psi in the presence of platinum oxide (Aldrich, 0.1 g) for 4 h. The catalyst was removed by filtration through Celite and the filtrate was concentrated to dryness. The residue was recrystallized from methanolethyl acetate-hexane to give 0.8 g (44%) of methyl 3-amino-5-hydroxymethyl-4-[(methylsulfonyl)amino]benzoate as a light brown powder, mp 150°–155° C.

Analysis: Calculated for $C_{10}H_{14}N_2O_5S$: C, 43.79; H, 5.14; N, 10.21 Found: C, 44.03; H, 5.14; N, 10.08

A mixture of methyl 3-amino-5-hydroxymethyl-4-(methylsulfonyl)aminobenzoate (0.548 g, 0.002 mol), 4N hydrochloric acid in dioxane (0.6 mL, 0.0024 mol), and cyanamide (0.84 g, 0.020 mol) in ethyl acetate (20 mL) was heated at reflux for 16 h. A brown-colored cake was deposited at the bottom of the flask. The supernatant was removed by decantation and the cake was stirred with fresh ethyl acetate (20 mL) at room temperature for 4 h. The brown solid was collected by filtration and dried to give 0.52 g (73%) of methyl 3-(aminoiminomethyl)amino-5-hydroxymethyl-4-(methylsulfonyl)aminobenzoate hydrochloride.

The above ester (9.5 g, 0.0014 mol) was stirred with 1N sodium hydroxide (3.0 mL, 0.003 mol) at room temperature for 16 h and the mixture filtered through a cotton plug. The filtrate was neutralized with concentrated hydrochloric acid. A fine yellow precipitate was obtained which was removed by filtration and the filtrate was evaporated to dryness. The residue was dissolved in methanol, insolubles removed by filtration, and the filtrate evaporated to dryness. The residue was again dissolved in methanol and 2-propanol was added. The precipitate which formed was collected by filtration and dried under vacuum over acetone reflux for 24 h to give 0.06 g (13%) of the title compound as a fluffy solid, mp 300°–307° C.

Analysis: Calculated for $C_{10}H_{14}N_4O_5S.H_2O.0.1[(CH_3)_2CH]_2O$: C, 38.52; H, 5.30; N, Found: C, 38.66; H, 5.16; N, 17.30

EXAMPLE 53

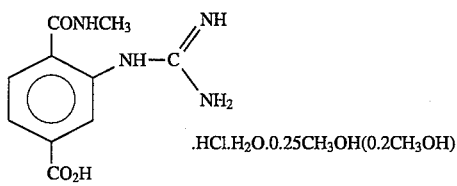

.$HCl.H_2O.0.25CH_3OH(0.2CH_3OH)$

3-[(Aminoiminomethyl)amino]-4-[(methylamino)carbonyl] benzoic acid hydrochloride, complex with water and methanol (4:4:4:1 and 5:5:5:1).

A mixture of nitroterephthalic acid (Aldrich, 20 g, 0.095 mol) in anhydrous methanol (100 mL) was heated to reflux in the presence of concentrated sulphuric acid (10 mL) for 1 h. The solvent was evaporated and the residue poured into saturated sodium bicarbonate (200 mL). The aqueous layer was washed with chloroform and 2N hydrochloric acid added to the aqueous layer to bring the pH close to 2. The mixture was extracted twice with ethyl acetate and the combined organic layers were washed with water and brine. The organic extract was concentrated after drying over sodium sulphate and the residue was recrystallized from ethyl acetate-hexane to give 11.8 g (55%) of 4-methoxycarbonyl-2-nitrobenzoic acid as cream-colored crystals, mp 131°–132° C.

Analysis: Calculated for $C_9H_7NO_6$: C, 48.01; H, 3.13; N, 6.22 Found: C, 47.97; H, 3.21; N, 6.16

A mixture of 4-methoxycarbonyl-2-nitrobenzoic acid (3.6 g, 0.016 mol) in thionyl chloride (32 mL) was heated to reflux in the presence of two drops of dimethylformamide for 3 h. Thionyl chloride was distilled and the concentrate was left under vacuum for 0.5 h. The residue was dissolved in dichloromethane (10 mL) and added to a solution of aqueous methylamine (40%, 2.0 g, 0.026 mol) in water (5 mL) over a period of 5 min. The mixture was further stirred for 10 min and the white precipitate was collected by filtration. The cake was washed with water, dried, and recrystallized from ethyl acetate-hexane to give 2.1 g (55%) of methyl 4-(methylamino)carbonyl-3-nitrobenzoate as white needles, mp 155° C.

Analysis: Calculated for $C_{10}H_{10}N_2O_5$: C, 50.42; H, 4.23; N, 11.76 Found: C, 50.54; H, 4.20; N, 11.89

A mixture of methyl 4-(methylamino)carbonyl-3-nitrobenzoate (3.84 g, 0.0185 mol) and tin (ii) chloride (15.3 g, 0.08 mol) in ethanol (80 mL) was heated at 70° C. for 1 h. The reaction mixture was diluted with water (150 mL) and sodium bicarbonate solution was added to it to bring the pH close to 8. The mixture was extracted with ethyl acetate and the organic layer washed with water and brine and dried over sodium sulphate. After filtration, the solution was concentrated and the residue was recrystallized from ethyl acetate-hexane to give 2.16 g (64%) of methyl 3-amino-4-(methylamino)carbonylbenzoate as tan needles, mp 167°–168° C.

Analysis: Calculated for $C_{10}H_{12}N_2O_3$: C, 57.68; H, 5.81; N, 13.45 Found: C, 57.81; H, 5.83; N, 13.50

A mixture of methyl 3-amino-4-(methylamino)carbonylbenzoate (0.624 g, 0.003 mol) and 1N sodium hydroxide (4.5 mol, 0.0045 mol) was stirred at room temperature for 4 h. The mixture was neutralized with concentrated hydrochloric acid and then acetic acid was added to bring the pH close to 3. The precipitate obtained was collected by filtration, washed with water, and dried under vacuum over acetone for 24 h to give 0.4 g (69%) of 3-amino-4-(methylamino)carbonylbenzoic acid as a pale yellow powder, mp 215°–217° C.

Analysis: Calculated for $C_9H_{10}N_2O_3$: C, 55.67; H, 5.19; N, 14.43 Found: C, 55.75; H, 5.25; N, 14.43

A mixture of 3-amino-4-(methylamino)carbonylbenzoic acid (0.194 g, 0.001 mol), concentrated hydrochloric acid (0.084 g, 0.001 mol), and cyanamide (0.588 g, 0.014 mol) in ethyl acetate (10 mL) was stirred at 37°–38° C. for 16 h. A white solid formed which was collected by filtration. Thin-layer chromatography showed the presence of the starting material. The white solid was again stirred at 37°–38° C. with cyanamide (0.42 g, 0.01 mol) in ethyl acetate (10 mL). A white solid was again collected by filtration and washed with ethyl acetate. It was recrystallized from methanol-ether to give 0.03 g (10%, first crop) of the title compound as white crystals, mp >300° C. A second crop (0.09 g, 30%) as white crystals, mp>300° C., was collected on allowing the filtrate to stand in the refrigerator for 2 days.

Analysis of first crop: Calculated for $C_{10}H_{12}N_4O_3 \cdot HCl \cdot H_2O \cdot 0.25$ MeOH: C, 41.21; H, 5.40; N, 18.76 Found: C, 41.14; H, 5.42; N, 18.98

Analysis of second crop: Calculated for $C_{10}H_{12}N_4O_3 \cdot HCl \cdot H_2O \cdot 0.2$MeOH: C, 41.23; H, 5.36; N, 18.86 Found: C, 41.48; H, 5.47; N, 19.20

Utility

The compounds of Formula (I) possess neuraminidase inhibitory activity and are therefore useful as antiviral and anti-microbial agents for the prevention, treatment, or amelioration of infections. More particularly, the compounds of Formula (I) possess influenza virus neuraminidase inhibitory activity and are effective as inhibitors of influenza infections. The neuraminidase inhibitory activity of the compounds of the present invention is demonstrated using standard assays of neuraminidase activity; for example, using the assay described below.

A fluorimetric assay was used to measure influenza virus neuraminidase activity. It utilized a substrate (2'-(4-methylumbelliferyl)-α-D-acetylneuraminic acid), which was cleaved by neuraminidase to yield a fluorescent product which was quantified. The assay mixture contained a compound of Formula (I) at various concentrations and an amount of neuraminidase in the form of whole virus or crystals in an appropriate buffer, at pH 6.5. The reaction was started by the addition of the substrate to a final concentration of 75 μM. After 5 min at 37° C., glycine and NaOH, pH 10.2, was added to terminate the reaction. A blank was run using the same substrate but no enzyme. Fluorescence was read using a fluorescence spectrophotometer (excitation: 360 nm and emission: 450 nM) and substrate blanks were subtracted from the readings. A compound was considered to be active if it had a percent inhibition value of more than about 10% for the inhibition of neuraminidase activity. The neuraminidase inhibitory activity of representative compounds of the invention is shown below in Table 1:

TABLE 1

Neuraminidase Inhibition as Determined by In Vitro Enzyme Assay

| Example No. | % Inhibition at 7 nM | IC$_{50}$ (mM) |
|---|---|---|
| 1 | 44 | — |
| 3 | 75 | 5.5 |
| 4 | 39 | — |
| 6 | 30 | — |
| 7 | 32 | — |
| 9 | 56 @ 3.3 mM | — |
| 10 | — | 1 |
| 16 | 34 | — |
| 17 | 00 | 5 |

TABLE 1-continued

Neuraminidase Inhibition as Determined by In Vitro Enzyme Assay

| Example No. | % Inhibition at 7 nM | IC$_{50}$ (mM) |
|---|---|---|
| 18 | 68 | — |
| 21 | — | 4 |
| 23 | 22 @ 3.5 mM | — |
| 26 | 15 | — |
| 27 | 27 | — |
| 31 | 31 | — |
| 33 | 42 | — |
| 35 | 25 | 20 |
| 36 | 35 | — |
| 37 | 28 | 14 |
| 39 | — | 0.0025 |
| 40 | — | 1 |
| 42 | — | 5.5 |
| 43 | — | 0.1 |
| 44 | — | 2 |
| 46 | 46 | — |
| 47 | 33 | — |
| 49 | — | 1.5 |
| 50 | — | 2 |
| 51 | — | 0.8 |
| 52 | — | 2 |
| 53 | — | 0.005 |

Dosage and Formulation

The antiviral compounds of this invention can be administered as treatment for viral infections by any means that produces contact of the active agent with the agent's site of action, the viral neuraminidase, in the body of a mammal. They can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage administered will, of course, vary depending upon known factors, such as the pharmacodynamic characteristics of the particular agent and its mode and route of administration; the age, health, and weight of the recipient; the nature and extent of the symptoms, the kind of concurrent treatment; the frequency of treatment; and the effect desired. A daily dosage of active ingredient can be expected to be about 0.001 to 1000 milligram (mg) per killigram (kg) of body weight, with the preferred dose being 0.1 to about 30 mg/kg.

Dosage forms (compositions suitable for administration) contain from about 1 mg to about 100 mg of active ingredient per unit. In these pharmaceutical compositions, the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms. Other dosage forms are potentially possible such as administration transdermally, via a patch mechanism or ointment.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar-coated or film-coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water-soluble salt of the active ingredient, suitable stabilizing agents, and, if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences,* Mack Publishing Company, a standard reference text in this field.

Useful pharmaceutical dosage forms for administration of the compounds of this invention can be illustrated as follows:

Capsules

A large number of unit capsules are prepared by filling standard two-piece hard gelatin capsules each with 100 mg of powdered active ingredient, 150 mg of lactose, 50 mg of cellulose, and 6 mg of magnesium stearate.

Soft Gelatin Capsules

A mixture of active ingredient in a digestible oil such as soybean oil, cottonseed oil, or olive oil is prepared and injected by means of a positive displacement pump into gelatin to form soft gelatin capsules containing 100 mg of the active ingredient. The capsules are washed and dried.

Tablets

A large number of tablets are prepared by conventional procedures so that the dosage unit was 100 mg of active ingredient, 0.2 mg of colloidal silicon dioxide, 5 mg of magnesium stearate, 275 mg of microcrystalline cellulose, 11 mg of starch, and 98.8 mg of lactose. Appropriate coatings may be applied to increase palatability or delay absorption.

Various modifications of the invention in addition to those shown and described herein will be apparent to those skilled in the art from the foregoing description. Such modifications are also intended to fall within the scope of the appended claims.

The foregoing disclosure includes all the information deemed essential to enable those skilled in the art to practice the claimed invention. Because the cited applications may provide further useful information, these cited materials are hereby incorporated by reference in their entirety.

What is claimed is:

1. A method for the treatment of infections caused by viral influenza, said method comprising the step of:

administering to a host in need of such treatment a pharmaceutically-effective amount of a compound of the Formula (I):

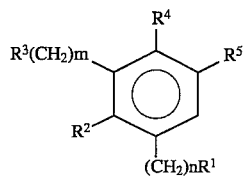

or pharmaceutically-suitable salts or prodrug forms thereof, wherein:

n is 0–1;
m is 0–3;
p is 0–1;
$R^1$ is selected from the group consisting of —$CO_2H$, —$SO_2H$, —$SO_3H$, —$PO_3H_2$, and tetrazolyl; provided that n is 1 when $R^1$ is other than $SO_2H$;
$R^2$ is selected from the group consisting of H, —OH, and —$NH_2$;
$R^3$ is selected independently at each occurrence from the group consisting of —OR, —$N(R)_2$, —$N_3$, —NHC($R^6$)$NH_2$, —CN, —C($R^6$)$NH_2$, H, —C(R)(=N)NHC(=NH)$NH_2$, —C(=N)RC(=NH)$NH_2$, NHCN, and CH=NOH;
$R^4$ is selected from the group consisting of H, —OR, —$(CH_2)_p$$NHR^7$, and —C(O)$NHR^8$;
$R^5$ is selected from the group consisting of H, —(CH($R^3$))$_n$$_m$$CH_2R^3$, —NHC($R^6$)$NH_2$, —CH=CH$CH_2R^3$, and CH=NOH;
$R^6$ is selected from the group consisting of =NH, =NOH, =NCN, =O, and =S;
$R^7$ is selected from the group consisting of —C(=Y)$R^8$, —S($O_2$)R, —C(O)$OR^8$, —C(=Y)$NHR^8$, and —$CH_2$C(=Y)$R^8$;
$R^8$ is selected from the group consisting of $C_1$–$C_4$ linear or branched alkyl substituted with 0–3 halogens on each carbon;
R is selected from the group consisting of H, $C_1$–$C_4$ linear or branched alkyl, $C_1$–$C_4$ linear or branched alkyl-OH, $C_1$–$C_4$ linear or branched alkyl-$NH_2$; and
Y is O or S.

2. A method according to claim 1, wherein it is provided that:

(1) when $R^1$ is $CO_2H$, $SO_3H$, or $PO_3H_2$, and $R^4$ is $(CH_2)_p$$NHR^7$, then $R^2$, $R^3$, and $R^5$ cannot all be H; and (2) the number of substituents on the aromatic ring cannot exceed four.

3. A method for the treatment of infections caused by viral influenza, said method comprising the step of:

administering to a host in need of such treatment a pharmaceutically-effective amount of a compound of the Formula (I):

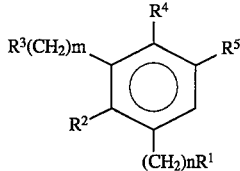

or pharmaceutically-suitable salts or prodrug forms thereof, wherein:

n is 0–1;
m is 0–3;
p is 0–1;
$R^1$ is selected from the group consisting of —$CO_2H$, —$SO_2H$, —$SO_3H$, —$PO_3H_2$, and tetrazolyl;
$R^2$ is selected from the group consisting of H, —OH, and —$NH_2$;

$R^3$ is selected independently at each occurrence from the group consisting of —OR, —N(R)$_2$, —N$_3$, —NHC(R$^6$)NH$_2$, —CN, —C(R$^6$)NH$_2$, —C(R)(=N)NHC(=NH)NH$_2$, —C(=N)RC(=NH)NH$_2$, NHCN, and CH=NOH; provided that when $R^3$ is —OR, R is selected from the group consisting of $C_1$–$C_4$ branched alkyl;

$R^4$ is selected from the group consisting of H, —OR, —(CH$_2$)$_p$NHR$^7$, and —C(O)NHR$^8$;

$R^5$ is selected from the group consisting of H, —(CH(R$^3$)$_n$)$_m$CH$_2$R$^3$, —NHC(R$^6$)NH$_2$, —CH=CHCH$_2$R$^3$, and CH=NOH;

$R^6$ is selected from the group consisting of =NH, =NOH, =NCN, =O, and =S;

$R^7$ is selected from the group consisting of —C(=Y)R$^8$, —S(O$_2$)R, —C(O)OR$^8$, —C(=Y)NHR$^8$, and —CH$_2$C(=Y)R$^8$;

$R^8$ is selected from the group consisting of $C_1$–$C_4$ linear or branched alkyl substituted with 0–3 halogens on each carbon;

R is selected from the group consisting of H, $C_1$–$C_4$ linear or branched alkyl, $C_1$–$C_4$ linear or branched alkyl-OH, $C_1$–$C_4$ linear or branched alkyl-NH$_2$; and Y is O or S.

4. A compound according to claim 3, wherein it is provided that:

(1) when $R^1$ is CO$_2$H, SO$_3$H, or PO$_3$H$_2$, and $R^4$ is (CH$_2$)$_p$NHR$^7$, then $R^2$, $R^3$, and $R^5$ cannot all be H; and (2) the number of substituents on the aromatic ring cannot exceed four.

5. A method for the treatment of infections caused by viral influenza, said method comprising the step of:

administering to a host in need of such treatment a pharmaceutically-effective amount of a compound of the Formula (I):

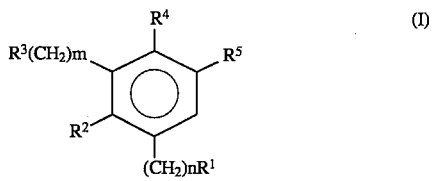

or pharmaceutically-suitable salts or prodrug forms thereof, wherein:

n is 0–1;
m is 0–3;
p is 0–1;

$R^1$ is selected from the group consisting of —CO$_2$H, —SO$_2$H, —SO$_3$H, —PO$_3$H$_2$, and tetrazolyl;

$R^2$ is selected from the group consisting of H, —OH, and —NH$_2$;

$R^3$ is selected independently at each occurrence from the group consisting of —OR, —N(R)$_2$, —N$_3$, —NHC(R$^6$)NH$_2$, —CN, —C(R$^6$)NH$_2$, H, —C(R)(=N)NHC(=NH)NH$_2$, —C(=N)RC(=NH)NH$_2$, NHCN, and CH=NOH;

$R^4$ is selected from the group consisting of H, —(CH$_2$)$_p$NHR$^7$, —C(O)NHR$^8$, —OH, —OCH$_3$, and —CONHCH$_3$; provided that when p=0 and $R^7$=C(=O)R$^8$, $R^8$ is a $C_4$ linear or branched alkyl substituted with 0–3 halogens on each carbon;

$R^5$ is selected from the group consisting of H, —(CH(R$^3$)$_n$)$_m$CH$_2$R$^3$, —NHC(R$^6$)NH$_2$, —CH=CHCH$_2$R$^3$, and CH=NOH;

$R^6$ is selected from the group consisting of =NH, =NOH, =NCN, =O, and =S;

$R^7$ is selected from the group consisting of —C(=Y)R$^8$, —S(O$_2$)R, —C(O)OR$^8$, —C(=Y)NHR$^8$, and —CH$_2$C(=Y)R$^8$;

$R^8$ is selected from the group consisting of $C_1$–$C_4$ linear or branched alkyl substituted with 0–3 halogens on each carbon;

R is selected from the group consisting of H, $C_1$–$C_4$ linear or branched alkyl, $C_1$–$C_4$ linear or branched alkyl-OH, $C_1$–$C_4$ linear or branched alkyl-NH$_2$; and Y is O or S.

6. A method according to claim 5, wherein it is provided that:

(1) when $R^1$ is CO$_2$H, SO$_3$H, or PO$_3$H$_2$, and $R^4$ is (CH$_2$)$_p$NHR$^7$, then $R^2$, $R^3$, and $R^5$ cannot all be H; and (2) the number of substituents on the aromatic ring cannot exceed four.

7. A method for the treatment of infections caused by viral influenza, said method comprising the step of:

administering to a host in need of such treatment a pharmaceutically-effective amount of a compound of the Formula (I):

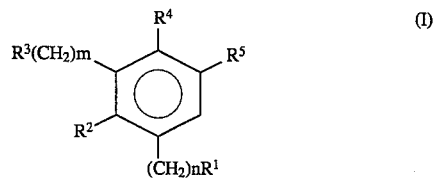

or pharmaceutically-suitable salts or prodrug forms thereof, wherein:

n is 0–1;
m is 0–3;
p is 0–1;

$R^1$ is selected from the group consisting of —CO$_2$H, —SO$_2$H, —SO$_3$H, —PO$_3$H$_2$, and tetrazolyl, provided that n is 1 when $R^1$ is other than SO$_2$H;

$R^2$ is selected from the group consisting of H, —OH, and —NH$_2$;

$R^3$ is selected independently at each occurrence from the group consisting of —OR, —N(R)$_2$, —N$_3$, —NHC(R$^6$)NH$_2$, —CN, —C(R$^6$)NH$_2$, H, —C(R)(=N)NHC(=NH)NH$_2$, —C(=N)RC(=NH)NH$_2$, NHCN, and CH=NOH;

$R^4$ is selected from the group consisting of H, —OR, —(CH$_2$)$_p$NHR$^7$, and —C(O)NHR$^8$;

$R^5$ is selected from the group consisting of —(CH(R$^3$)$_n$)$_m$CH$_2$R$^3$, —NHC(R$^6$)NH$_2$, —CH=CHCH$_2$R$^3$, CH=NOH, CH$_2$OR, NHCN; provided that when $R^5$ is CH$_2$OR, R is not H; that $R^3$ in not H; that when $R^3$ is OR, R is not H; and that when $R^3$ is N(R)$_2$, R is not H;

$R^6$ is selected from the group consisting of =NH, =NOH, =NCN, =O, and =S;

$R^7$ is selected from the group consisting of —C(=Y)R$^8$, —S(O$_2$)R, —C(O)OR$^8$, —C(=Y)NHR$^8$, and —CH$_2$C(=Y)R$^8$;

$R^8$ is selected from the group consisting of $C_1$–$C_4$ linear or branched alkyl substituted with 0–3 halogens on each carbon;

R is selected from the group consisting of H, $C_1$–$C_4$ linear or branched alkyl, $C_1$–$C_4$ linear or branched alkyl-OH, $C_1$–$C_4$ linear or branched alkyl-NH$_2$; and Y is O or S.

8. A method according to claim 7, wherein it is provided that:

(1) when $R^1$ is CO$_2$H, SO$_3$H, or PO$_3$H$_2$, and $R^4$ is (CH$_2$)$_p$NHR$^7$, then $R^2$, $R^3$, and $R^5$ cannot all be H; and (2) the number of substituents on the aromatic ring cannot exceed four.

9. A method for the treatment of infections caused by viral influenza, said method comprising the step of:

administering to a host in need of such treatment a pharmaceutically-effective amount of a compound of the Formula (I):

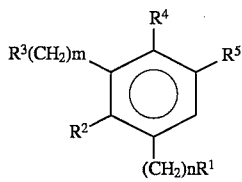

or pharmaceutically-suitable salts or prodrug forms thereof, wherein:

n is 0–1;
m is 0–3;
p is 0–1;
$R^1$ is tetrazolyl;
$R^2$ is selected from the group consisting of H, —OH, and —$NH_2$;
$R^3$ is selected from the group consisting of —$N_3$, amidine, substituted amidines, hydroxyamidine, substituted hydroxyamidines, cyanoamidine, substituted cyanoamidines, urea, substituted ureas, thiourea, substituted thioureas, —C(R)(=N)NHC(=NH)$NH_2$, —C(=N)RC(=NH)$NH_2$, —NHCN, and —CH=NOH;
$R^4$ is selected from the group consisting of —NHC(=S)$R^8$, and —C(O)$NHR_8$;
$R^5$ is the same as $R^3$;
$R^8$ is selected from the group consisting of $C_1$–$C_4$ linear or branched alkyl substituted with 0–3 halogens on each carbon;
R is selected from the group consisting of H, $C_1$–$C_4$ linear or branched alkyl, $C_1$–$C_4$ linear or branched alkyl-OH, $C_1$–$C_4$ linear or branched alkyl-$NH_2$.

10. A method according to claim 9, wherein it is provided that:

(1) when $R^1$ is $CO_2H$, $SO_3H$, or $PO_3H_2$, and $R^4$ is $(CH_2)_pNHR^7$, then $R^2$, $R^3$, and $R^5$ cannot all be H; and
(2) the number of substituents on the aromatic ring cannot exceed four.

11. A method according to claim 1, including administering said compound according to Formula I or pharmaceutically-acceptable salts or prodrugs thereof, wherein:

$R^1$ is —$CO_2H$;
$R^2$ is H;
$R^3$ is selected from the group consisting of —H, —OR, —NHC($R^6$)$NH_2$, and CH=NOH;
$R^4$ is selected from the group consisting of H, —OR, —$(CH_2)_pNHR^7$, and —C(O)$NHR^8$;
$R^5$ is selected from the group consisting of H, —$(CH(R^3)_2)_mCH_2OR$, —$CH_2OR$, —NHC($R^6$)$NH_2$, —CH=CH$CH_2$OR, —NHCN, and CH=NOH;
$R^6$ is selected from the group consisting of =NH, =NOH, =NCN, =O, and =S;
$R^7$ is selected from the group consisting of —C(=Y)$R^8$, —S($O_2$)R, —C(O)$OR^8$, —C(=Y)$NHR^8$, and —$CH_2C$(=Y)$R^8$;
$R^8$ is selected from the group consisting of $C_1$–$C_4$ linear or branched alkyl substituted with 0–3 halogens on each carbon;
m is 0–2;
with the following provisos:
(1) when $R^1$ is $CO_2H$ is $(CH_2)_pNHR^7$, then $R^2$, $R^3$, and $R^5$ cannot all be H; and
(2) the number of substituents on the aromatic ring cannot exceed four.

12. A method according to claim 3, including administering said compound according to Formula I or pharmaceutically-acceptable salts or prodrugs thereof, wherein:

$R^1$ is —$CO_2H$;
$R^2$ is H;
$R^3$ is selected from the group consisting of —H, —OR, —NHC($R^6$)$NH_2$, and CH=NOH;
$R^4$ is selected from the group consisting of H, —OR, —$(CH_2)_pNHR^7$, and —C(O)$NHR^8$;
$R^5$ is selected from the group consisting of H, —$(CH(R^3)_2)_mCH_2OR$, —$CH_2OR$, —NHC($R^6$)$NH_2$, —CH=CH$CH_2$OR, —NHCN, and CH=NOH;
$R^6$ is selected from the group consisting of =NH, =NOH, =NCN, =O, and =S;
$R^7$ is selected from the group consisting of —C(=Y)$R^8$, —S($O_2$)R, —C(O)$OR^8$, —C(=Y)$NHR^8$, and —$CH_2C$(=Y)$R^8$;
$R^8$ is selected from the group consisting of $C_1$–$C_4$ linear or branched alkyl substituted with 0–3 halogens on each carbon;
m is 0–2;
with the following provisos:
(1) when $R^4$ is $(CH_2)_pNHR^7$, then $R^2$, $R^3$, and $R^5$ cannot all be H; and
(2) the number of substituents on the aromatic ring cannot exceed four.

13. A method according to claim 5, including administering said compound according to Formula I or pharmaceutically-acceptable salts or prodrugs thereof, wherein:

$R^1$ is —$CO_2H$;
$R^2$ is H;
$R^3$ is selected from the group consisting of —H, —OR, —NHC($R^6$)$NH_2$, and CH=NOH;
$R^4$ is selected from the group consisting of H, —OR, —$(CH_2)_pNHR^7$, and —C(O)$NHR^8$;
$R^5$ is selected from the group consisting of H, —$(CH(R^3)_2)_mCH_2OR$, —$CH_2OR$, —NHC($R^6$)$NH_2$, —CH=CH$CH_2$OR, —NHCN, and CH=NOH;
$R^6$ is selected from the group consisting of =NH, =NOH, =NCN, =O, and =S;
$R^7$ is selected from the group consisting of —C(=Y)$R^8$, —S($O_2$)R, —C(O)$OR^8$, —C(=Y)$NHR^8$, and —$CH_2C$(=Y)$R^8$;
$R^8$ is selected from the group consisting of $C_1$–$C_4$ linear or branched alkyl substituted with 0–3 halogens on each carbon;
m is 0–2;
with the following provisos:
(1) when $R^4$ is $(CH_2)_pNHR^7$, then $R^2$, $R^3$, and $R^5$ cannot all be H; and
(2) the number of substituents on the aromatic ring cannot exceed four.

14. A method according to claim 7, including administering said compound according to Formula I or pharmaceutically-acceptable salts or prodrugs thereof, wherein:

$R^1$ is —$CO_2H$;
$R^2$ is H;

$R^3$ is selected from the group consisting of —H, —OR, —NHC($R^6$)NH$_2$, and CH=NOH;

$R^4$ is selected from the group consisting of H, —OR, —(CH$_2$)$_p$NHR$^7$, and —C(O)NHR$^8$;

$R^5$ is selected from the group consisting of H, —(CH(R$^3$)$_2$)$_m$CH$_2$OR, —CH$_2$OR, —NHC(R$^6$)NH$_2$, —CH=CHCH$_2$OR, —NHCN, and CH=NOH;

$R^6$ is selected from the group consisting of =NH, =NOH, =NCN, =O, and =S;

$R^7$ is selected from the group consisting of —C(=Y)R$^8$, —S(O$_2$)R, —C(O)OR$^8$, —C(=Y)NHR$^8$, and —CH$_2$C(=Y)R$^8$;

$R^8$ is selected from the group consisting of C$_1$–C$_4$ linear or branched alkyl substituted with 0–3 halogens on each carbon;

m is 0–2;

with the following provisos:
(1) when R$^1$ is CO$_2$H is (CH$_2$)$_p$NHR$^7$, then R$^2$, R$^3$, and R$^5$ cannot all be H; and
(2) the number of substituents on the aromatic ring cannot exceed four.

15. A method according to claim 9, including administering said compound according to Formula I or pharmaceutically-acceptable salts or prodrugs thereof, wherein:

$R^2$ is H;

$R^3$ is selected from the group consisting of —H, —OR, —NHC(R$^6$)NH$_2$, and CH=NOH;

$R^4$ is selected from the group consisting of H, —OR, —(CH$_2$)$_p$NHR$^7$, and —C(O)NHR$^8$;

$R^5$ is selected from the group consisting of H, —(CH(R$^3$)$_2$)$_m$CH$_2$OR, —CH$_2$OR, —NHC(R$^6$)NH$_2$, —CH=CHCH$_2$OR, —NHCN, and CH=NOH;

$R^6$ is selected from the group consisting of =NH, =NOH, =NCN, =O, and =S;

$R^7$ is selected from the group consisting of —C(=Y)R$^8$, —S(O$_2$)R, —C(O)OR$^8$, —C(=Y)NHR$^8$, and —CH$_2$C(=Y)R$^8$;

$R^8$ is selected from the group consisting of C$_1$–C$_4$ linear or branched alkyl substituted with 0–3 halogens on each carbon;

m is 0–2;

with the following provisos:
(1) when R$^1$ is CO$_2$H is (CH$_2$)$_p$NHR$^7$, then R$^2$, R$^3$, and R$^5$ cannot all be H; and
(2) the number of substituents on the aromatic ring cannot exceed four.

16. A method according to claim 1, including administering said compound according to Formula I or pharmaceutically-acceptable salts or prodrugs thereof, wherein:

$R^1$ is —CO$_2$H;

$R^2$ is H;

$R^3$ is selected from the group consisting of —H, —OH, —NHC(=NH)NH$_2$, and CH=NOH;

$R^4$ is selected from the group consisting of H, —OH, —NHCOCH$_3$, —NHSO$_2$CH$_3$, and —C(O)NHCH$_3$;

$R^5$ is selected from the group consisting of H, —CH$_2$CH(OH)CH$_2$OH, —CH$_2$OH, —NHC(=NH)NH$_2$, —NHC(=NCN)NH$_2$, —CH=CHCH$_2$OH, —NHCN, and CH=NOH;

m is 0–2;

with the following provisos:
(1) when R$^1$ is CO$_2$H and R$^4$ is (CH$_2$)$_p$NHR$^7$, then R$^2$, R$^3$, and R$^5$ cannot all be H; and
(2) the number of substituents on the aromatic ring cannot exceed four.

17. A method according to claim 3, including administering said compound according to Formula I or pharmaceutically-acceptable salts or prodrugs thereof, wherein:

$R^1$ is —CO$_2$H;

$R^2$ is H;

$R^3$ is selected from the group consisting of —H, —OH, —NHC(=NH)NH$_2$, and CH=NOH;

$R^4$ is selected from the group consisting of H, —OH, —(CH$_2$)$_p$NHR$^7$, —NHCOCH$_3$, —NHSO$_2$CH$_3$, and —C(O)NHCH$_3$;

$R^5$ is selected from the group consisting of H, —CH$_2$CH(OH)CH$_2$OH, —CH$_2$OH, —NHC(=NH)NH$_2$, —NHC(=NCN)NH$_2$, —CH=CHCH$_2$OH, —NHCN, and CH=NOH;

m is 0–2;

with the following provisos:
(1) when R$^1$ is CO$_2$H and R$^4$ is (CH$_2$)$_p$NHR$^7$, then R$^2$, R$^3$, and R$^5$ cannot all be H; and
(2) the number of substituents on the aromatic ring cannot exceed four.

18. A method according to claim 5, including administering said compound according to Formula I or pharmaceutically-acceptable salts or prodrugs thereof, wherein:

$R^1$ is —CO$_2$H;

$R^2$ is H;

$R^3$ is selected from the group consisting of —H, —OH, —NHC(=NH)NH$_2$, and CH=NOH;

$R^4$ is selected from the group consisting of H, —OH, —(CH$_2$)$_p$NHR$^7$, —NHCOCH$_3$, —NHSO$_2$CH$_3$, and —C(O)NHCH$_3$;

$R^5$ is selected from the group consisting of H, —CH$_2$CH(OH)CH$_2$OH, —CH$_2$OH, —NHC(=NH)NH$_2$, —NHC(=NCN)NH$_2$, —CH=CHCH$_2$OH, —NHCN, and CH=NOH;

m is 0–2;

with the following provisos:
(1) when R$^1$ is CO$_2$H and R$^4$ is (CH$_2$)$_p$NHR$^7$, then R$^2$, R$^3$, and R$^5$ cannot all be H; and
(2) the number of substituents on the aromatic ring cannot exceed four.

19. A method according to claim 7, including administering said compound according to Formula I or pharmaceutically-acceptable salts or prodrugs thereof, wherein:

$R^1$ is —CO$_2$H;

$R^2$ is H;

$R^3$ is selected from the group consisting of —H, —OH, —NHC(=NH)NH$_2$, and CH=NOH;

$R^4$ is selected from the group consisting of H, —OH, —NHCOCH$_3$, —NHSO$_2$CH$_3$, and —C(O)NHCH$_3$;

$R^5$ is selected from the group consisting of H, —CH$_2$CH(OH)CH$_2$OH, —CH$_2$OH, —NHC(=NH)NH$_2$, —NHC(=NCN)NH$_2$, —CH=CHCH$_2$OH, —NHCN, and CH=NOH;

m is 0–2;

with the following provisos:
(1) when R$^1$ is CO$_2$H and R$^4$ is (CH$_2$)$_p$NHR$^7$, then R$^2$, R$^3$, and R$^5$ cannot all be H; and
(2) the number of substituents on the aromatic ring cannot exceed four.

20. A method according to claim 9, including administering said compound according to Formula I or pharmaceutically-acceptable salts or prodrugs thereof, wherein:

$R^2$ is H;

$R^3$ is selected from the group consisting of —H, —OH, —NHC(=NH)NH$_2$, and CH=NOH;

$R^4$ is selected from the group consisting of H, —OH, —NHCOCH$_3$, —NHSO$_2$CH$_3$, and —C(O)NHCH$_3$;

$R^5$ is selected from the group consisting of H, —CH$_2$CH(OH)CH$_2$OH, —CH$_2$OH, —NHC(=NH)NH$_2$, —NHC(=NCN)NH$_2$, —CH=CHCH$_2$OH, —NHCN, and CH=NOH;

m is 0–2;

with the following provisos:
(1) when $R^1$ is CO$_2$H and $R^4$ is (CH$_2$)$_p$NHR$^7$, then $R^2$, $R^3$, and $R^5$ cannot all be H; and
(2) the number of substituents on the aromatic ring cannot exceed four.

21. A method for the treatment of infections caused by viral influenza, said method comprising the step of:

administering to a host in need of such treatment a pharmaceutically-effective amount of a compound selected from the group consisting of:
Phenylguanidine;
1-Phenylbiguanide;
4-Acetylaminobenzoic acid;
2-Acetylaminobenzenesulfonic acid;
4-Acetylaminophenylphosphoric acid;
4-(Trifluoroacetamido)benzoic acid;
4-Thioacetamidobenzoic acid;
4-[(Methylsulfonyl)amino]benzoic acid;
3-Guanidinobenzoic acid;
3-[Amino(cyanoimino)methyl]aminobenzoic acid;
3-Cyanoaminobenzoic acid;
3-(2-Amino-2-imino)ethylbenzoic acid;
4-(Acetamino)phenylacetic acid;
4-(Methylaminocarbonyl)benzoic acid;
4-Acetylamino-3-hydroxymethylbenzoic acid;
β-(2-N-Acetylamino-5-carboxyphenyl)ethanol;
4-Acetylamino-3-(2',3'-dihydroxypropyl)benzoic acid;
4-Acetylamino-3-aminobenzoic acid;
4-Acetylamino-3-[(aminoiminomethyl)amino]benzoic acid;
3-[(Aminoiminomethyl)amino]-4-(2-methylpropionylamino)benzoic acid;
4-Acetylamino-3-[(hydroxylimino)methyl]benzoic acid;
3-[(Aminoiminomethyl)amino]-4-[(methylsulfonyl)amino]benzoic acid;
3-[(N-Hydroxyimino)methyl]-4-[(methylsulfonyl)amino]benzoic acid;
3-[((Aminoimino)methyl)amino]-4-methoxybenzoic acid;
3-[(Aminoiminomethyl)amino]-4-hydroxybenzoic acid;
3,5-Bis-[(aminoiminomethyl)amino]benzoic acid;
3-Amino-5-{[(aminoimino)methyl]amino}benzoic acid;
3-[(Aminoiminomethyl)amino]-5-[(N-hydroxylimino)methyl]benzoic acid; and
3-[(Aminoiminomethyl)amino-5-hydroxymethyl)-4-(methylsulfonyl)aminobenzoic acid.

22. A pharmaceutical composition comprising a pharmaceutically-suitable carrier and a therapeutically-effective antiviral amount of a compound according to the Formula (I):

$$\begin{array}{c} R \quad H \quad NH_2 \\ | \quad | \quad | \\ -C=N-N-C=NH \end{array}$$

$$\begin{array}{c} NH \\ \| \\ -C=N-R-C-NH_2 \end{array}$$

or pharmaceutically-suitable salts or prodrug forms thereof, wherein:

n is 0–1;

m is 0–3;

p is 0–1;

$R^1$ is tetrazolyl;

$R^2$ is selected from the group consisting of H, —OH, and —NH$_2$;

$R^3$ is selected from the group consisting of —N$_3$, —N(R)$_2$, —CN, —C(R$^6$)NH$_2$, —NHC(R$_6$)NH$_2$, —C(R)(=N)NHC(=NH)NH$_2$, —C(=N)RC(=NH)NH$_2$, —NHCN, and —CH=NOH;

$R^4$ is selected from the group consisting of —NHC(=S)R$^8$, and —C(O)NHR$^8$;

$R^5$ is the same as $R^3$;

$R^6$ is selected from the group consisting of =NH, =NOH, =NCN, =O, and =S;

$R^8$ is selected from the group consisting of C$_1$–C$_4$ linear or branched alkyl substituted with 0–3 halogens on each carbon;

R is selected from the group consisting of H, C$_1$–C$_4$ linear or branched alkyl, C$_1$–C$_4$ linear or branched alkyl-OH, C$_1$–C$_4$ linear or branched alkyl-NH$_2$.

23. A compound of the Formula (I):

or pharmaceutically-suitable salts or prodrug forms thereof, wherein:

n is 0–1;

m is 0;

$R^1$ is —CO$_2$H;

$R^2$ is selected from the group consisting of H, —OH, and —NH$_2$;

$R^3$ is H;

$R^4$ is —C(O)NHR$^8$;

$R^5$ is —NHC(R$^6$)NH$_2$ $R^6$ is selected from the group consisting of =NH, =NOH, =NCN, =O, and =S; and $R^8$ is selected from the group consisting of C$_1$–C$_4$ linear or branched alkyl substituted with 0–3 halogens on each carbon.

24. A method for the treatment of infections caused by viral influenza, said method comprising the step of:

administering to a host in need of such treatment a pharmaceutically-effective amount of a compound of claim 23.

25. pharmaceutical composition comprising a pharmaceutically-suitable carrier and a therapeutically-effective antiviral amount of a compound according to claim 23.

* * * * *